US012419938B2

(12) United States Patent
Kenyon et al.

(10) Patent No.: US 12,419,938 B2
(45) Date of Patent: Sep. 23, 2025

(54) PROENZYME COMPOSITION

(71) Applicant: Propanc Pty Ltd, Camberwell (AU)

(72) Inventors: Julian Kenyon, Camberwell (AU);
Ralf Brandt, Camberwell (AU)

(73) Assignee: Propanc Pty Ltd, Camberwell (AU)

( * ) Notice: Subject to any disclaimer, the term of this patent is extended or adjusted under 35 U.S.C. 154(b) by 0 days.

(21) Appl. No.: 15/775,375

(22) PCT Filed: Nov. 11, 2016

(86) PCT No.: PCT/AU2016/051082
§ 371 (c)(1),
(2) Date: May 10, 2018

(87) PCT Pub. No.: WO2017/079802
PCT Pub. Date: May 18, 2017

(65) Prior Publication Data
US 2019/0262435 A1    Aug. 29, 2019

Related U.S. Application Data

(60) Provisional application No. 62/321,377, filed on Apr. 12, 2016.

(30) Foreign Application Priority Data

Nov. 12, 2015 (AU) .................... 2015904678

(51) Int. Cl.
*A61K 38/48* (2006.01)
*A61K 9/00* (2006.01)
*A61P 35/00* (2006.01)

(52) U.S. Cl.
CPC ........ *A61K 38/4826* (2013.01); *A61K 9/0019* (2013.01); *A61P 35/00* (2018.01); *C12Y 304/21001* (2013.01); *C12Y 304/21004* (2013.01)

(58) Field of Classification Search
CPC ... A61K 38/4826; A61K 9/0019; A61P 35/00; C12Y 304/21001; C12Y 304/21004
USPC ..................................................... 424/94.64
See application file for complete search history.

(56) References Cited

U.S. PATENT DOCUMENTS

| 4,514,388 | A | 4/1985 | Psaledakis |
| 4,978,332 | A | 12/1990 | Luck et al. |
| 5,595,756 | A | 1/1997 | Bally et al. |
| 5,858,357 | A | 1/1999 | Trnka et al. |
| 6,670,330 | B1 | 12/2003 | Lampidis et al. |
| 9,636,359 | B2 | 5/2017 | Kenyon et al. |
| 2004/0018987 | A1 | 1/2004 | Hoffman et al. |
| 2004/0167079 | A1 | 8/2004 | Tidmarsh |
| 2005/0026852 | A1 | 2/2005 | Rustum et al. |
| 2007/0031398 | A1 | 2/2007 | Miller |

FOREIGN PATENT DOCUMENTS

| EP | 1 426 047 A1 | 6/2004 |
| EP | 1 652 519 A1 | 5/2006 |
| KR | 2007-0012040 A | 1/2007 |
| RU | 2149021 C1 | 5/2000 |
| WO | 2004/062604 A2 | 7/2004 |
| WO | 2009/061051 A1 | 5/2009 |
| WO | WO 2011/047434 A1 | 4/2011 |
| WO | WO 2015/070828 A1 | 5/2015 |
| WO | 2017/177270 A1 | 10/2017 |

OTHER PUBLICATIONS

Beuth, et al., (Jun. 2001) "Impact of complementary oral enzyme application on the postoperative treatment results of breast cancer patients—results of an epidemiological multicentre retrolective cohort study", Cancer Chemotherapy and Pharmacology, 47(Suppl. 1):S45-S54.
Chabner, et al., (Jan. 1, 2005) "Chemotherapy and the war on cancer", Nature Reviews Cancer, 5:65-72.
Cohen, et al., (Nov. 5, 1999) "Oral Enzyme Therapy and Experimental Rat Mammary Tumor Metastasis", Life Sciences, 65(24):2603-2614.
Dreyer, et al., (Dec. 1, 1955) "The Activation of Chymotrypsinogen Isolation and Identification of a Peptide Liberated during Activation", Journal of Biological Chemistry, 217(2):527-540.
Gonzalez, et al., (1999) "Evaluation of Pancreatic Proteolytic Enzyme Treatment of Adenocarcinoma of the Pancreas, With Nutrition and Detoxification Support", Nutrition and Cancer, 33(2):117-124.
Gura, (Nov. 7, 1997) "Systems for Identifying New Drugs are Often Faulty", Science, 278(5340):1041-1042.
Gurkoff, et al., (Apr. 1974) "Preliminary Study on the Effects of Combined Hydrolytic Enzyme Agents on Mouse Krebs-2 Carcinoma", Journal of the American Osteopathic Association, 73(8):672-673.
Jiang, et al., (Dec. 1999) "Selenium-Induced Inhibition of Angiogenesis in Mammary Cancer at Chemopreventive Levels of Intake", Molecular Carcinogenesis, 26(4):213-225.
Keller, et al., (1958) "The Proteins of Bovine Pancreatic Juice", The Journal of Biological Chemistry, 233(2):344-349.
Leipner, et al., (Apr. 2000) "Systemic Enzyme Therapy in Oncology Effect and Mode of Action", Drugs, 59(4):769-780.
Merchan, et al., (Oct. 2010) "Antiangiogenic Activity of 2-Deoxy-D-Glucose", Plos One, 5(10):e13699.
Peran, et al., (Oct. 25, 2017) "A Formulation of Pancreatic Pro-Enzymes Provides Potent Anti-Tumour Efficacy: A Pilot Study Focused on Pancreatic and Ovarian Cancer", Scientific Reports, 7(1):13998, pp. 1-15.

(Continued)

*Primary Examiner* — Jennifer M. H. Tichy
(74) *Attorney, Agent, or Firm* — Lee & Hayes, P.C.

(57) ABSTRACT

The present invention relates to compositions, methods, uses and kits for treating cancer. In particular, the invention relates to compositions and methods of treating cancer in a subject comprising administering chymotrypsinogen in certain amounts, for example greater than about 0.1 mg/kg, and trypsinogen in an amount, for example, greater than about 0.02 mg/kg, thereby treating cancer. The invention also relate to compositions and methods for treating cancer in a subject comprising chymotrypsinogen and trypsinogen wherein the weight ratio of chymotrypsinogen:trypsinogen is greater than 8:1.

4 Claims, 20 Drawing Sheets

(56) References Cited

OTHER PUBLICATIONS

Popiela, et al., (Jun. 2001) "Influence of a Complementary Treatment with Oral Enzymes on Patients with Colorectal Cancers—an Epidemiological Retrolective Cohort Study", Cancer Chemotherapy and Pharmacology, 47(Suppl. 1): S55-S63.

Pyun, et al., (Jan. 1, 2008) "Capsiate, a Nonpungent Capsaicin-Like Compound, Inhibits Angiogenesis and Vascular Permeability via a Direct Inhibition of Src Kinase Activity", Cancer Research, 68(1):227-235.

Saruc, et al., (May 2004) "Pancreatic Enzyme Extract Improves Survival in Murine Pancreatic Cancer", Pancreas, 28(4):401-412.

Wald, et al., (Jul. 2001) "Mixture of Trypsin, Chymotrypsin and Papain Reduces Formation of Metastases and Extends Survival Time of C57BI6 Mice with Syngeneic Melanoma B16", Cancer Chemotherapy and Pharmacology, 47(Suppl. 1):S16-S22.

Wald, et al., (1998) "Polyenzyme Preparation Wobe-Mugos® Inhibits Growth of Solid Tumors and Development of Experimental Metastases in Mice", Life Sciences, 62(3):43-48.

Wald, et al., (Sep. 18, 1998) "Proteinases Reduce Metastatic Dissemination and Increase Survival Time in C57BI6 Mice with the Lewis Lung Carcinoma", Life Sciences, 63(17):237-43.

Novak, J.F. et al., Proenzyme Therapy of Cancer, Anticancer Research 2005, vol. 25, pp. 1157-1177.

Kaiserova, P. et al., Proenzyme Therapy of Sarcoma S-180 and Melanoma B16-F10, Journal of Applied Biomedecine 2014, vol. 12, No. 1, pp. 39-47.

Peran, M. et al., In Vitro Treatment of Carcinoma Cell Lines with Pancreatic (pro)enzymes Suppresses the EMT Programme and Promotes Cell Differentiation, Cellular Oncology 2013, vol. 36, No. 4, pp. 289-301.

International Search Report and Written Opinion for Application No. PCT/GB2016/050233 mailed on May 3, 2016.

Novak et al. (2006) "Trypsin/chymotrypsin and Their Respective Zymogens Inhibit Tumor Growth in Vitro and in Vivo", Cancer Research, 47:2 pages.

Yu et al., "Cancer stem cells", Int J Biochem Cell Biol, Dec. 2012;44(12):2144-51. doi: 10.1016/j.biocel.2012.08.022.

Zumiya et al. (2012) "Chemoresistance is Associated with Cancer Stem Cell-like Properties and Epithelial-to-Mesenchymal Transition in Pancreatic Cancer Cells". Anticancer Research, vol. 32, pp. 3847-3854.

Ju et al. (2014) "Maintenance of the stemness in CD44+ HCT-15 and HCT-116 human colon cancer cells requires miR-203 suppression". Stem Cell Research, vol. 12, pp. 86-100.

Lugli et al. (Juy 6, 2010) "Prognostic impact of the expression of putative cancer stem cell markers CD133, CD166, CD44s, EpCAM, and ALDHI in colorectal cancer". British Journal of Cancer, vol. 103, pp. 382-390.

Ozawa et al. (Jun. 12, 2014) "Prognostic significance of CD44 variant 2 upregulation in colorectal cancer". British Journal of Cancer, vol. 111, pp. 365-374.

Roy et al. (Jun. 2014) "Decreased Camptothecin Sensitivity of the Stem-Cell-Like Fraction of Caco2 Cells Correlates with an Altered Phosphorylation Pattern of Topoisomerase I". PLOS One, vol. 9(6), e99628, pp. 1-11.

Reya et al. (Nov. 2001). "Stem cells, cancer, and cancer stem cells" . . . Nature, vol. 414(6859), pp. 105-111.

Figure 1: Mean Body Weight ± SEM (g) for Each Group During Study #1

Figure 2: Mean Body Weight ± SEM (g) for Each Group During Study #2

Group 1 (PBS, 10 ml/kg, daily i.v) Day 26

Figure 5:
Group 2 (T:C, 27.5 mg/kg:165 mg/kg) Day 26
   
5862359     5865983     5872646     5875516
   
5878042     5885211     5888253     5890091
5897691
1 cm Group 3 (T:C, 83.3 mg/kg:500 mg/kg) Day 26

Figure 8
3710961  3712594  3713507  3718011  3722791
3723439  3724287  3726283  3733385  3735781
3739074  3742064
10 mm Figure 9
| 3710299 | 3716411 | 3718487 | 3718829 | 3724380 |
| 3725382 | 3728913 | 3731980 | 3732762 | 3736767 |
3741335   3743600
10 mm

Figure 11
            
3707810     3711377     3711536     3712927     3729006
            
3729939     3732583     3741870     3744980     3745235
3746406
10 mm

PROENZYME COMPOSITION

CROSS REFERENCES TO RELATED APPLICATIONS

The present application is a National Stage Application, filed under 35 U.S.C. § 371, of International Application No. PCT/AU2016/051082, filed Nov. 11, 2016, which claims priority from Australian provisional application No. 2015904678, filed Nov. 12, 2015, and U.S. provisional No. 62/321,377, filed Apr. 12, 2016, the entire contents of both applications are hereby incorporated by reference in their entireties.

FIELD OF THE INVENTION

The present invention relates to compositions, methods, uses and kits for treating cancer.

BACKGROUND OF THE INVENTION

The use of proteases in treating cancer has been suggested for some time. Initially fresh pancreatic enzyme extracts was contemplated as a possible cancer therapy and some successful experiments were conducted with Jersen's mouse sarcoma model. After injecting the mouse with the protease enzyme trypsin, a regression of tumours was observed. The results obtained produced great interest, and crude enzyme extracts prepared from sheep pancreas were used to treat human cancer patients to reduce tumour progression and prolong survival time.

The use of proenzymes (inactive precursor form of enzymes) has been used to try to overcome problems encountered with the oral administration of enzymes with mixed results. A proenzyme mixture including trypsinogen, which is the proenzyme form of the serine protease inhibitor trypsin, has been shown to be useful in treating carcinomas and believed to be selectively activated at the surface of tumour cells. The mechanism of action of trypsin is believed to occur by way of proteolysis of the tumour cells. A composition including chymotrypsinogen and trypsinogen has been shown to be effective in assays for cancer, including pancreatic cancer and colon cancer (WO 2011/047434).

However, there exists a need to provide new or improved cancer treatments.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a composition for treating cancer comprising chymotrypsinogen, trypsinogen and a pharmaceutically acceptable diluent, excipient or carrier, wherein the composition is adapted to administer chymotrypsinogen in an amount of equal to, or greater than, 0.1 mg/kg and trypsinogen in an amount of equal to, or greater than, 0.02 mg/kg.

The invention also provides a composition for treating cancer in a subject comprising chymotrypsinogen and trypsinogen wherein the composition comprises chymotrypsinogen in an amount of greater than 1 mg/kg and trypsinogen in an amount of greater than 0.2 mg/kg.

In any aspect of the invention, the composition comprises or consists of chymotrypsinogen and trypsinogen, wherein the amount of chymotrypsinogen is greater than 1.5 mg/kg, 2 mg/kg, 3.5 mg/kg, 5 mg/kg, 15 mg/kg, 20 mg/kg, 40 mg/kg, 45 mg/kg, 135 mg/kg, 250 mg/kg or 500 mg/kg. The amount of chymotrypsinogen and trypsinogen may be equal to, or greater than, any mg/kg value described herein, including in Tables 1, 4, 8, 10 and the Examples, particularly Example 5.

In any aspect of the invention, the composition for treating cancer in a human comprises or consists of chymotrypsinogen and trypsinogen, wherein the amount of chymotrypsinogen is greater than 0.1 mg/kg, 0.15 mg/kg, 0.25 mg/kg, 0.4 mg/kg, 1.2 mg/kg, 3.5 mg/kg, 10 mg/kg, 20 mg/kg or 40 mg/kg. The amount of chymotrypsinogen and trypsinogen may be equal to, or greater than, any mg/kg value described herein, particularly Example 5.

In any aspect of the invention, the composition comprises or consists of chymotrypsinogen and trypsinogen, wherein the amount of trypsinogen is greater than 0.25 mg/kg, 0.4 mg/kg, 0.6 mg/kg, 0.8 mg/kg, 2 mg/kg, 2.5 mg/kg, 3 mg/kg, 5 mg/kg, 7 mg/kg, 8 mg/kg, 20 mg/kg, 40 mg/kg or 80 mg/kg. The amount of chymotrypsinogen and trypsinogen may be equal to, or greater than, any mg/kg value described herein, including in Tables 1, 4, 8, 10 and the Examples, particularly Example 5.

In any aspect of the invention, the composition for treating cancer in a human comprises or consists of chymotrypsinogen and trypsinogen, wherein the amount of trypsinogen is greater than 0.02 mg/kg, 0.03 mg/kg, 0.05 mg/kg, 0.06 mg/kg, 0.2 mg/kg, 0.6 mg/kg, 1.5 mg/kg, 3 mg/kg or 6 mg/kg. The amount of chymotrypsinogen and trypsinogen may be equal to, or greater than, any mg/kg value described herein, particularly Example 5.

The invention provides a pharmaceutical composition for treating cancer in a subject comprising chymotrypsinogen, trypsinogen and a pharmaceutically acceptable diluent, excipient or carrier, wherein the composition comprises chymotrypsinogen in an amount of greater than 1 mg/kg and trypsinogen in an amount of greater than 0.2 mg/kg, or any other amount as described herein, particularly Example 5. In one embodiment, the only active anti-tumour ingredients present in the composition are chymotrypsinogen and trypsinogen.

The invention provides a pharmaceutical composition for treating cancer in a subject comprising as active ingredients chymotrypsinogen and trypsinogen, the composition further comprising a pharmaceutically acceptable diluent, excipient or carrier, wherein the composition comprises chymotrypsinogen in an amount of greater than 1 mg/kg and trypsinogen in an amount of greater than 0.2 mg/kg, or any other amount as described herein, particularly Example 5. In one embodiment, the only active anti-tumour ingredients present in the composition are chymotrypsinogen and trypsinogen.

The invention provides a pharmaceutical composition for treating cancer in a subject comprising as main ingredients chymotrypsinogen and trypsinogen, the composition further comprising a pharmaceutically acceptable diluent, excipient or carrier, wherein the composition comprises chymotrypsinogen in an amount of greater than 1 mg/kg and trypsinogen in an amount of greater than 0.2 mg/kg, or any other amount as described herein, particularly Example 5. In one embodiment, the only active anti-tumour ingredients present in the composition are chymotrypsinogen and trypsinogen.

The invention provides a pharmaceutical composition for treating pancreatic cancer in a subject comprising chymotrypsinogen, trypsinogen and a pharmaceutically acceptable diluent, excipient or carrier, wherein the composition comprises chymotrypsinogen in an amount of at least greater than 10 mg/kg, preferably greater than 13 mg/kg, and trypsinogen in an amount of greater than 1.5 mg/kg, preferably greater than 2 mg/kg. Preferably, chymotrypsinogen in an amount of, or no more than, 41 mg/kg and trypsinogen in an amount of, or no more than, 7 mg/kg.

The invention provides a pharmaceutical composition for treating ovarian cancer in a subject comprising chymotrypsinogen, trypsinogen and a pharmaceutically acceptable diluent, excipient or carrier, wherein the composition comprises chymotrypsinogen in an amount of greater than 3 mg/kg, preferably greater than 4 mg/kg, and trypsinogen in an amount of greater than 0.4 mg/kg, preferably greater than 0.7 mg/kg. Preferably, chymotrypsinogen in an amount of, or no more than, 13 mg/kg and trypsinogen in an amount of, or no more than, 2.2 mg/kg.

The invention also provides a pharmaceutical composition for use in treating cancer in a subject comprising chymotrypsinogen, trypsinogen and a pharmaceutically acceptable diluent, excipient or carrier, wherein the composition comprises chymotrypsinogen in an amount of greater than 1 mg/kg and trypsinogen in an amount of greater than 0.2 mg/kg, or any other amount as described herein, particularly Example 5.

The invention also provides a pharmaceutical composition comprising chymotrypsinogen, trypsinogen and a pharmaceutically acceptable diluent, excipient or carrier for use in treating cancer in a subject, wherein the composition comprises chymotrypsinogen in an amount of greater than 1 mg/kg and trypsinogen in an amount of greater than 0.2 mg/kg, or any other amount as described herein, particularly Example 5.

The present invention also provides a unit dose composition comprising chymotrypsinogen and trypsinogen, wherein the unit dose is adapted to administer chymotrypsinogen in an amount of greater than, or equal to, 6 mg/kg and trypsinogen in an amount of greater than, or equal to, 1 mg, or any other amount as described herein. Preferably, chymotrypsinogen is in an amount of greater than, or equal to, 9 mg, 15 mg, 24 mg, 72 mg, 210 mg, 600 mg, 1200 mg, 2400 mg. Preferably, trypsinogen is in an amount of greater than or equal to 1.5 mg, 3 mg, 3.5 mg, 12 mg, 36 mg, 90 mg, 180 mg or 360 mg.

The present invention also provides a composition for use in treating cancer, the composition comprising trypsinogen at a concentration of 0.25 mg/ml and chymotrypsinogen at a concentration of 1.5 mg/ml. Preferably, trypsinogen is in a concentration of 4.3, 8.7 or 30 mg/ml and chymotrypsinogen is in a concentration of 25, 50 or 100 mg/ml. Trypsinogen and chymotrypsinogen may be in any other concentration as described herein such as those in the Examples.

In any aspect of the invention, the pharmaceutical composition comprises, consists of, or is adapted to administer, chymotrypsinogen and trypsinogen, wherein the amount of chymotrypsinogen is greater than 1.5 mg/kg, 2 mg/kg, 3.5 mg/kg, 5 mg/kg, 15 mg/kg, 20 mg/kg, 40 mg/kg, 45 mg/kg, 135 mg/kg, 250 mg/kg or 500 mg/kg. The amount of chymotrypsinogen and trypsinogen may be equal to, or greater than, any mg/kg value described herein, including in Tables 1, 4, 8, 10 and the Examples, particularly Example 5.

In any aspect of the invention, the pharmaceutical composition for human use comprises, consists of, or is adapted to administer chymotrypsinogen and trypsinogen, wherein the amount of chymotrypsinogen is greater than 0.1 mg/kg, 0.15 mg/kg, 0.25 mg/kg, 0.4 mg/kg, 1.2 mg/kg, 3.5 mg/kg, 10 mg/kg, 20 mg/kg or 40 mg/kg. The amount of chymotrypsinogen may be equal to, or greater than, any mg/kg value described herein, particularly Example 5.

In any aspect of the invention, the pharmaceutical composition comprises, consists of, or is adapted to administer, chymotrypsinogen and trypsinogen, wherein the amount of trypsinogen administered is greater than 0.25 mg/kg, 0.4 mg/kg, 0.6 mg/kg, 0.8 mg/kg, 2 mg/kg, 2.5 mg/kg, 3 mg/kg, 5 mg/kg, 7 mg/kg, 8 mg/kg, 20 mg/kg, 40 mg/kg or 80 mg/kg. The amount of trypsinogen may be equal to, or greater than, any mg/kg value described herein, including in Tables 1, 4, 8, 10 and the Examples.

In any aspect of the invention, the pharmaceutical composition for human use comprises, consists of, or is adapted to administer chymotrypsinogen and trypsinogen, wherein the amount of trypsinogen administered is greater than 0.02 mg/kg, 0.03 mg/kg, 0.05 mg/kg, 0.06 mg/kg, 0.2 mg/kg, 0.6 mg/kg, 1.5 mg/kg, 3 mg/kg or 6 mg/kg. The amount of trypsinogen may be equal to, or greater than, any mg/kg value described herein, particularly Example 5.

The present invention includes a method of treating cancer in a subject comprising administering chymotrypsinogen in an amount of greater than 1 mg/kg and trypsinogen in an amount of greater than 0.2 mg/kg, thereby treating cancer.

In any method of the invention, the amount of chymotrypsinogen administered in a single dose or in multiple doses over the period of a 24 hour period is greater than 1 mg/kg but less than 500 mg/kg.

In any method of the invention, the amount of trypsinogen administered in a single dose or in multiple doses over the period of a 24 hour period is at least greater than 0.2 mg/kg but less than 90 mg/kg.

The present invention provides a method of treating cancer in a subject comprising administering chymotrypsinogen in an amount of 500 mg/kg and trypsinogen in an amount of 83 mg/kg, thereby treating cancer. Preferably, the cancer is pancreatic cancer or ovarian cancer. Even more preferably, the pancreatic cancer is an adenocarcinoma.

The present invention provides a method of treating cancer in a human comprising administering chymotrypsinogen in an amount of 40 mg/kg and trypsinogen in an amount of 7 mg/kg, thereby treating cancer. Preferably, the cancer is pancreatic cancer. Even more preferably, the pancreatic cancer is an adenocarcinoma.

The present invention provides a method of treating cancer in a human comprising administering chymotrypsinogen in an amount of 4 mg/kg or 13 mg/kg and trypsinogen in an amount of 0.7 mg/kg or 2 mg/kg, thereby treating cancer. Preferably, the cancer is ovarian cancer.

In any method of the invention, the administration of the amount of trypsinogen and chymotrypsinogen does not result in any clinically observable adverse event in the subject 1 week after administration, 1 day after administration, or preferably 1 hour after administration. The clinically observable adverse event may be any one or more of weight loss, reddening at site of injection and behavioural changes, or any other event described herein, particularly the Examples.

In any aspect of the invention, chymotrypsinogen and trypsinogen is administered in a weight ratio in the range of at or about 1:1 to at or about 10:1, at or about 4:1 to at or about 8:1, at or about 5:1 to at or about 7:1, or at about 6:1. Further, any composition described above has chymotrypsinogen and trypsinogen in a weight ratio in the range of at or about 1:1 to at or about 10:1, at or about 4:1 to at or about 8:1, at or about 5:1 to at or about 7:1, or at about 6:1 The present invention also provides use of chymotrypsinogen and trypsinogen in the manufacture of a medicament for the treatment of cancer, wherein the medicament is adapted to administer chymotrypsinogen in an amount of greater than 1 mg/kg and trypsinogen in an amount of greater than 0.2 mg/kg, or any other amount as described herein, particularly Example 5.

The invention also provides a kit for treating cancer comprising at least one dosage unit, wherein the dosage unit comprises chymotrypsinogen, trypsinogen and a pharmaceutically acceptable diluent, excipient or carrier, wherein the dosage unit is adapted to administer chymotrypsinogen and trypsinogen equal to, or greater than, any amount or mg/kg value described herein, including in Tables 1, 4, 8 and 10, particularly Example 5.

Optionally the kit also includes written instructions directing the user to administer a dosage unit of chymotrypsinogen in an amount of greater than 1 mg/kg and trypsinogen in an amount of greater than 0.2 mg/kg, or any other amount as described herein, particularly Example 5.

The methods and pharmaceutical compositions of the invention are useful for treating cancers and metastatic carcinomas including pancreatic cancer, oesophageal cancer, colon cancer, bowel cancer, prostate cancer, ovarian cancer, brain cancer, stomach cancer, breast cancer, liver cancer, malignant melanoma or lung cancer.

Preferably, the cancer is pancreatic cancer, colon cancer or ovarian cancer. More preferably, the cancer is pancreatic cancer.

In any aspect of a method or use of the invention, the method or use further comprises the step of identifying a subject having, or at risk of developing, cancer. Preferably, the cancer is any one described herein.

In any aspect of the invention, the composition does not contain or the method or use does not administer, amylase.

In any aspect, embodiment or form of the invention described herein the amount of chymotrypsinogen administered may be greater than, or equal to, 1 mg/kg, 1.5 mg/kg, 2 mg/kg, 3.5 mg/kg, 5 mg/kg, 15 mg/kg, 20 mg/kg, 40 mg/kg, 45 mg/kg, 135 mg/kg, 250 mg/kg or 500 mg/kg. The chymotrypsinogen administered may be equal to, or greater than, any mg/kg value described herein, including in Tables 1, 4, 8 and 10, particularly Example 5.

In any aspect, embodiment or form of the invention described herein the amount of trypsinogen administered may be greater than, or equal to, 0.2 mg/kg, 0.25 mg/kg, 0.4 mg/kg, 0.6 mg/kg, 0.8 mg/kg, 2 mg/kg, 2.5 mg/kg, 3 mg/kg, 5 mg/kg, 7 mg/kg, 8 mg/kg, 20 mg/kg, 40 mg/kg or 80 mg/kg. The trypsinogen administered may be equal to, or greater than, any mg/kg value described herein, including in Tables 1, 4, 8 and 10, particularly Example 5.

In any aspect, embodiment or form of the invention described herein the amount of chymotrypsinogen administered to a human may be greater than, or equal to, 0.1 mg/kg, 0.15 mg/kg, 0.25 mg/kg, 0.4 mg/kg, 1.2 mg/kg, 3.5 mg/kg, 10 mg/kg, 20 mg/kg or 40 mg/kg. The amount of chymotrypsinogen may be equal to, or greater than, any mg/kg value described herein, particularly Example 5.

In any aspect, embodiment or form of the invention described herein the amount of trypsinogen administered to a human may be greater than, or equal to, 0.02 mg/kg, 0.03 mg/kg, 0.05 mg/kg, 0.06 mg/kg, 0.2 mg/kg, 0.6 mg/kg, 1.5 mg/kg, 3 mg/kg or 6 mg/kg. The amount of trypsinogen may be equal to, or greater than, any mg/kg value described herein, particularly Example 5.

Preferably, in any aspect, embodiment or form of the invention described herein the amount of chymotrypsinogen administered may be in the range of 1 mg/kg to 41 mg/kg, 1.5 mg/kg to 500 mg/kg, 2 mg/kg to 250 mg/kg, 3.5 mg/kg to 135 mg/kg, 5 mg/kg or 15 mg/kg to 45 mg/kg. The chymotrypsinogen administered may be in a range of between any two mg/kg values described herein, including in Tables 1, 4, 8, 10 and the Examples, particularly Example 5.

Preferably, in any aspect, embodiment or form of the invention described herein the amount of trypsinogen administered may be greater than 0.2 mg/kg to 7 mg/kg, 0.25 mg/kg to 80 mg/kg, 0.4 mg/kg to 40 mg/kg, 0.6 mg/kg to 20 mg/kg, 0.8 mg/kg to 8 mg/kg, or 2.5 mg/kg to 8 mg/kg. The trypsinogen administered may be in a range of between any two mg/kg values described herein, including in Tables 1, 4, 8, 10 and the Examples, particularly Example 5.

In any composition of the invention above, the composition may be adapted to administer the relevant mg, or mg/kg, of chymotrypsinogen and trypsinogen to the subject.

The invention also provides, any aspect of the invention above including values are 'about' the stated value above. For example, a further aspect of the invention is any of the aspects above where reference to 500 mg/kg is about 500 mg/kg. This is contemplated for all aspects or embodiments of the invention and for all values.

The invention provides a composition for treating cancer in a subject comprising chymotrypsinogen and trypsinogen wherein the weight ratio of chymotrypsinogen:trypsinogen is greater than 8:1 (i.e. 8 or more:1). Preferably, the weight ratio is greater than 10:1. Preferably, the weight ratio is 10:1. The weight ratio may be 8:1, 10:1 or between 8:1 and 10:1. In any of the embodiments, the composition preferably does not contain amylase, i.e. it comprises administration of an amylase-free composition.

The present invention provides a method of treating cancer in a subject comprising administering chymotrypsinogen and trypsinogen, wherein the weight ratio of chymotrypsinogen:trypsinogen is greater than 8:1, thereby treating cancer in the subject. Preferably, the weight ratio is greater than 10:1. Preferably, the weight ratio is 10:1. The weight ratio may be 8:1, 10:1 or between 8:1 and 10:1. In one embodiment, the method does not comprise the administration of amylase, i.e. it comprises administration of an amylase-free composition.

The present invention provides use of chymotrypsinogen and trypsinogen, in the manufacture of a medicament for the treatment of cancer, wherein the weight ratio of chymotrypsinogen:trypsinogen is greater than 8:1. Preferably, the weight ratio is greater than 10:1. Preferably, the weight ratio is 10:1. The weight ratio may be 8:1, 10:1 or between 8:1 and 10:1. In one embodiment, the medicament does not comprise amylase.

Preferably, the cancer is any one or more of pancreatic cancer, oesophageal cancer, colon cancer, bowel cancer, prostate cancer, ovarian cancer, stomach cancer, breast cancer, liver cancer, malignant melanoma, fibrosarcoma or lung cancer. Preferably, the cancer is ovarian, melanoma, brain, prostate, colorectal, liver or lung. Preferably, the cancer is pancreatic cancer, colon cancer or ovarian cancer. More preferably, the cancer is pancreatic cancer.

In any aspect of the invention, chymotrypsinogen and trypsinogen is administered intravenously, subcutaneously or intramuscularly.

In any aspect of the invention, chymotrypsinogen and trypsinogen may be administered simultaneously or sequentially.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 5: Images of excised tumours from mice in Group 2 (T:C, 27.5 mg/kg:165 mg/kg) Day 26 in study described in Example 3 performed to assess anti-tumour efficacy of Trypsinogen and Chymotrypsinogen A, administered in combination against Pan02 mouse pancreatic cancer cells, orthotopically inoculated in female C57BL/6 mice.

FIG. 8: Images of excised tumours at study termination for Group 2: Vehicle Control (PBS) in study described in Example 4 performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice.

FIG. 9: Images of excised tumours at study termination for Group 3: Trypsinogen/Chymotrypsinogen A, 83.3/500 mg/kg in study described in Example 4 performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice.

FIG. 11: Images of excised tumours at study termination for Group 5: Trypsinogen/Chymotrypsinogen A, 9.1/54 mg/kg in study described in Example 4 performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice.

DETAILED DESCRIPTION OF THE EMBODIMENTS

Figure 1:
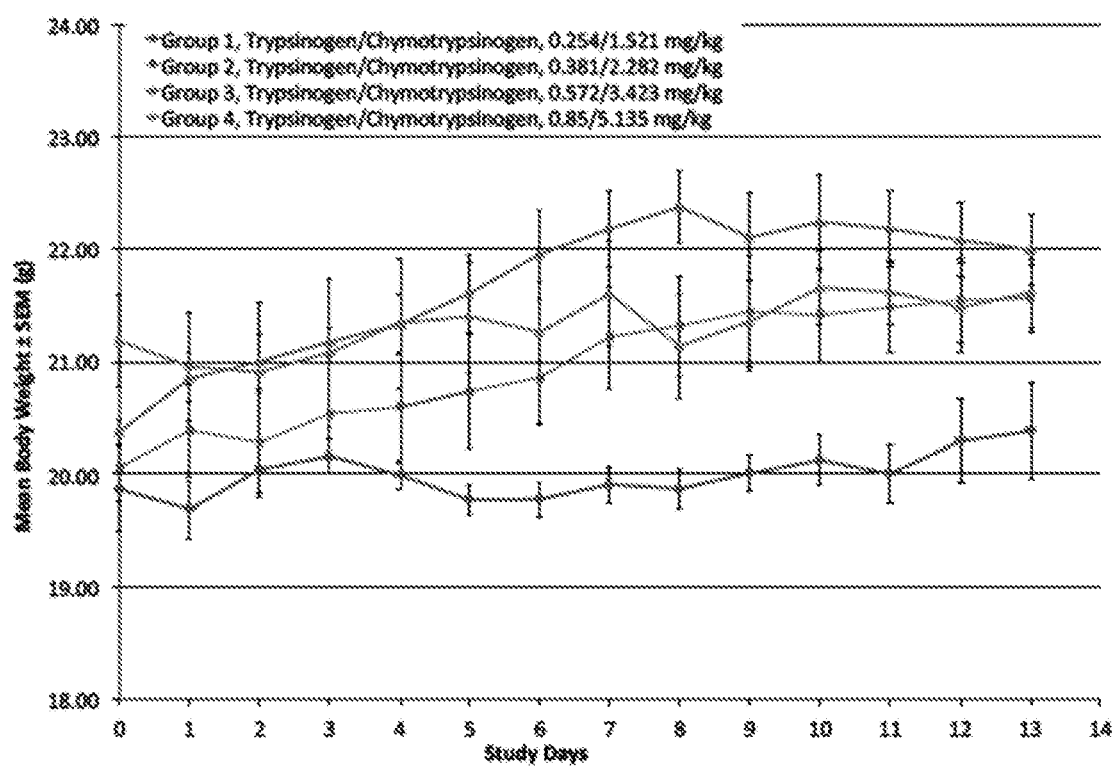
FIG. 1: Mean Body Weight±SEM (g) for Each Group During Study #1. Treatments were administered as single i.v. injection, once daily for seven consecutive days. Treatment was initiated to each group in a staggered manner, beginning with the lowest dose and then increasing the dose on each subsequent day. For all data calculations and presentation, the first day of treatment for each group is designated as Study Day 0.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The present invention is based on the surprising finding that chymotrypsinogen and trypsinogen can be administered at amounts significantly higher than previously used. This could occur in a single administration, or over a period of a single day. Surprisingly, these significantly higher amounts of chymotrypsinogen and trypsinogen, even hundred fold higher amounts, can be administered without any significant adverse clinical events. In addition, these higher amounts are shown to reduce the weight of several tumour types in vivo. The present invention provides an important benefit in the treatment of cancer as a larger effective dose of chymotrypsinogen and trypsinogen can be safely administered than previously used thereby providing a greater therapeutic window.

Chymotrypsinogen (which may be abbreviated to 'C' herein) is a proenzyme form of the enzyme chymotrypsin, which preferentially cleaves proteins at the following amino acids: tyrosine, tryptophan, phenylalanine and leucine. Chymotrypsin may be referred to or includes chymotrypsin A, chymotrypsin B (including B1 and B2 forms), chymotrypsin C, α-chymarophht, avazyme, chymar, chymotest, enzeon, quimar, quimotrase, α-chymar, α-chymotrypsin A, α-chymotrypsin. Chymotrypsin C can be formed from pig chymotrypsinogen C or from cattle subunit II of procarboxypeptidase A, and preferentially cleaves proteins at the following amino acids: tyrosine, tryptophan, phenylalanine, leucine, methionine, glutamine, and asparagine. Chymotrypsinogen includes chymotrypsinogen B1 and chymotrypsinogen B2.

Trypsinogen (which may be abbreviated to 'T' herein) is a proenzyme form of trypsin, which preferentially cleaves proteins at arginine and lysine. Trypsin may be referred to or include α-trypsin, β-trypsin, cocoonase, parenzyme, parenzymol, tryptar, trypure, pseudotrypsin, tryptase, tripcellim, sperm receptor hydrolase β-trypsin can be formed from trypsinogen by cleavage of one peptide bond. Further peptide bond cleavages produce a and other iso-forms. Multiple cationic and anionic trypsins can be isolated from the pancreas of many vertebrates and from lower species including crayfish, insects (cocoonase) and microorganisms (*Streptomyces griseus*). In normal processes during digestion, inactive trypsinogen is activated by enteropeptidase present in intestinal mucosa to form the enzyme trypsin, which being a serine protease then acts to cleave the peptide bonds on the carboxyl side of basic amino acids/proteins.

The trypsinogen and chymotrypsinogen used in any aspect of the invention may be isolated, purified, substantially purified, recombinant or synthetic.

The proenzymes trypsinogen and chymotrypsinogen may be precursors of the enzymes selected from chymotrypsin classes 3.4.21.1 or 3.4.21.2 or trypsin from class 3.4.21.4, or selected from any other suitable source (classes grouped according to the classification of the Nomenclature Committee of the International Union of Biochemistry and Molecular Biology). These enzymes are commercially available and may be of human, bovine or porcine origin.

As used herein, "any other amount as described herein" or "any mg/kg value described herein" includes any amount or mg/kg value described in any of the Examples including in Tables 1, 4, 8 and 10.

The present invention includes human conversions for all amounts in mg/kg referred to herein based on human body weights of 50, 60, 70, 80, 90, 100 or more kg and body surface area of 1.1, 1.2, 1.3, 1.4, 1.5, 1.6, 1.7, 1.8 or more m². Specifically, amounts per kg for human administration, and methods for calculation, are referred to in Example 5.

As mentioned, the proenzyme form essentially provides an inactivated form of the enzyme that becomes activated in situ (e.g in vivo or in vitro activation). For example, activation of the proenzyme (conversion of proenzyme to active enzyme) may occur on contact with the surface of the tumour cell. It is believed that the proenzymes trypsinogen and chymotrypsinogen are selectively activated into the enzymes trypsin and chymotrypsin on contact with tumour cells and not on contact with healthy cells. The use of proenzymes reduces problems associated with providing, in situ, an active enzyme, such as undesirable reactions or inactivation of the enzyme before reaching an intended target of a tumour cell.

In relation to tumour cells, protease enzymes can act to break down the cell wall of malignant cells by cleaving the amide bonds present in peptide chains of the cell walls (proteolysis). It is also understood that protease inhibitors, which are present in non-malignant cells and inhibit or reduce the effect of enzymes in breaking down cell walls, are absent in malignant tumour cells. In addition to providing proteolytic activity, the protease proenzymes can upregulate the expression of β-catenin and E-cadherin in tumour cells. Cell-to-cell adhesion is facilitated by complex formation or bonding between β-catenin and E-cadherin at the cell surface, and therefore increased expression of β-catenin and E-cadherin leads to enhanced cell-to-cell adhesion and thereby reducing metastasis of tumour cells. The protease proenzymes may also provide other cellular activity such as increased immunorecognition or differentiation.

A significant adverse event, experience or reaction is any untoward medical occurrence that at any dose: results in death, is life-threatening (places the subject at immediate risk of death), requires in subject/subject hospitalization or prolongation of existing hospitalization, results in persistent or significant disability, incapacity, or is a congenital anomaly/birth defect.

A clinically observable adverse event is any untoward medical occurrence in a subject or clinical investigation subject administered a pharmaceutical product. A clinically observable adverse event may include any one of the events or observations described herein, particularly in the Examples. Typically, the period of observation is about 1 week after administration, about 1 day after administration, or preferably about 1 hour after administration. The period of observation may be the time between administration of doses.

"Treating" or "treatment" refers to both therapeutic treatment and prophylactic or preventative measures, wherein the aim is to prevent, ameliorate, reduce or slow down (lessen) cancer or the spread (metastasis) thereof.

In any method of the invention, one or more of the following effects may be observed: reduction in the reoccurrence of malignant tumours, reduction in metastasis of malignant tumours, reduction in number or size of tumours, differentiation of tumour cells, expression of β-catenin and E-cadherin in malignant tumours to facilitate cell-to-cell adhesion and reduction in metastasis, reduction in tumour cells ability to prevent immunorecognition.

"Preventing", "prevention", "preventative" or "prophylactic" refers to keeping from occurring, or to hinder, defend from, or protect from the occurrence of a condition, disease, disorder, or phenotype, including an abnormality or symptom. A subject in need of prevention may be prone to develop the condition.

The term "ameliorate" or "amelioration" refers to a decrease, reduction or elimination of a condition, disease, disorder, or phenotype, including an abnormality or symptom. A subject in need of treatment may already have the condition, or may be prone to have the condition or may be one in whom the condition is to be prevented.

The "subject" includes a mammal. The mammal may be a human, or may be a domestic, zoo, or companion animal. While it is particularly contemplated that the methods of the invention are suitable for medical treatment of humans, they are also applicable to veterinary treatment, including treatment of companion animals such as dogs and cats, and domestic animals such as horses, cattle and sheep, or zoo animals such as felids, canids, bovids, and ungulates. A subject may be afflicted with cancer or other disorder, or may not be afflicted with cancer or other disorder (i.e., free of detectable disease).

The typical body weight of a human subject may be greater than, or equal to, 60, 65, 70, 75, 80, 85, 90, 95, 100, 105 or 110 kg.

The term "therapeutically effective amount" refers to an amount of composition, or agent or compound in the composition, capable of treating, preventing or ameliorating cancer or the spread (metastasis) thereof. A therapeutically effective amount may be determined empirically and in a routine manner in relation to treating cancer, and will result in increased life expectancy.

As used herein "adapted to administer" refers to a composition that has the capacity to administer trypsinogen and chymotrypsinogen at the specified amount or concentration in a single dose or multiple doses.

As described herein, methods of the invention include treatment of neoplasms and related conditions, cancers, tumours, malignant and metastatic conditions. Tissues and organs associated with solid tumours and metastases which can be treated with a method or pharmaceutical composition of the invention include, but are not limited to, biliary tract, bladder, blood, brain, breast, cervix, colon, endometrium, esophagus, head, neck, kidney, larynx, liver, lung, medulla, melanin, ovarian, pancreas, prostate, rectum, renal, retina, skin, stomach, testes, thyroid, urinary tract, and uterus. The cancer may be a carcinoma and developed in an epithelium or from epithelial cells. The cancer may be a sarcoma and developed in connective tissue. The brain cancer may be glioblastoma.

The methods and pharmaceutical compositions of the invention are useful for treating cancers and metastatic carcinomas of the following types: pancreatic cancer, oesophageal cancer, colon cancer, bowel cancer, prostate cancer, ovarian cancer, stomach cancer, breast cancer, malignant melanoma or lung cancer. Preferably, the cancer is pancreatic cancer, colon cancer or ovarian cancer. More preferably, the cancer is pancreatic cancer. The metastatic carcinoma may have low, moderate or high metastatic potential.

The methods and pharmaceutical compositions of the invention may provide a multiple effect approach to treating cancer, for example by increasing in tumour cells apoptosis, cell-to-cell adhesion, differentiation and immunogenicity (targeting and removal by immune system). It is therefore beneficial to conduct treatment in the absence of any other treatments that may suppress or harm the immune system.

Methods or uses of the invention can be supplemented by other conventional anti-cancer therapeutic approaches directed to treatment or prevention of proliferative disorders (e.g., tumour). For example, such methods can be used in prophylactic cancer prevention, prevention of cancer recurrence and metastases after surgery, and as an adjuvant of other conventional cancer therapy.

The pharmaceutical compositions of the invention may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The pharmaceutical compositions of the invention may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. They may, for example, be administered in a form suitable for immediate release or extended release, for example, by the use of devices such as subcutaneous implants, encapsulated spheroids or osmotic pumps.

In addition to primates, such as humans, a variety of other mammals can be treated according to the methods of the tenth aspect. For instance, mammals including, but not limited to, cows, sheep, goats, horses, dogs, cats, guinea pigs, rats or other bovine, ovine, equine, canine, feline, rodent or murine species can be treated.

The term "pharmaceutically acceptable" as used herein means the carrier, diluent or excipient is not deleterious to the recipient thereof.

The terms "administration of and or "administering" should be understood to mean providing to an individual in need of treatment.

An individual in need of treatment may be one diagnosed with, or at risk of developing, any one of the cancers described herein.

The pharmaceutical compositions of the invention, and preparations or formulations thereof may be prepared by admixing together the components of the composition, namely chymotrypsinogen and trypsinogen. The admixing may be performed sequentially or simultaneously.

The pharmaceutical compositions of the invention may conveniently be presented in dosage unit form and may be prepared by any of the methods well known in the art of pharmacy. All methods include the step of bringing the active agents and protease proenzyme into association with the carrier which constitutes one or more accessory ingredients. In general, the pharmaceutical compositions are prepared by uniformly and intimately bringing the active agents and protease proenzymes into association with a liquid carrier or a finely divided solid carrier or both, and then, if necessary, shaping the product into the desired formulation. The active agents and protease proenzymes are provided in a dosage unit form in an amount sufficient to produce the desired effect upon the process or condition of diseases after single or repeated administration.

The pharmaceutical compositions of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the protease proenzyme and active agent of the first and second aspects in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the protease proenzyme and active agent of the first and second aspects are mixed with an inert solid diluent, for example, calcium carbonate, calcium phosphate or kaolin, or as soft gelatin capsules wherein the protease proenzyme and active agent of the first and second aspects are mixed with water or an oil medium, for example peanut oil, liquid paraffin, or olive oil.

Aqueous suspensions contain the active agent and protease proenzyme in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, n-methyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active agent and protease proenzyme in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These may be preserved by the addition of an anti-oxidant such as ascorbic acid.

Dispersible powders and granules suitable for preparation of an aqueous suspension by the addition of water provide the protease proenzyme and active agent of the first and second aspects in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally—occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy ethylene sorbitan monooleate. The emulsions may also contain sweetening and flavouring agents.

Syrups and elixirs may be formulated with sweetening agents, for example glycerol, propylene glycol, sorbitol or sucrose. They may also contain a demulcent, a preservative and flavoring and coloring agents.

The pharmaceutical compositions of invention may be in the form of a sterile injectable aqueous or oleagenous suspension. This suspension may be formulated according to the known art using those suitable dispersing or wetting agents and suspending agents which have been mentioned above. The pharmaceutical compositions of the first and second aspects may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In a particular embodiment, the pharmaceutical compositions of the invention are formulated as suppositories for rectal administration of the drug. These formulations can be prepared by mixing the protease proenzyme and active agent of the first and second aspects with a suitable non-irritating excipient which is solid at ordinary temperatures but liquid at the rectal temperature and will therefore melt in the rectum to release the drug. Such materials include cocoa butter and polyethylene glycols. Rectal administration may be used to elimate entero-hepatic first pass effect in the gastro-intestinal tract related to oral administration of enzymes.

The pharmaceutical compositions of the invention, may also be formulated in liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The liposome formulation may contain stabilisers, preservatives, excipients and the like. The preferred lipids are the phospholipids and phosphatidyl cholines, both natural and synthetic. Methods to form liposomes are known in the art.

The pharmaceutical compositions of the invention, may be included in a container, pack, or dispenser together with instructions for administration. The protease proenzymes and active agents, and optionally additional active agent, of the pharmaceutical composition may be provided as separated components in the container, pack, or dispenser, to be taken separately or together at the same or different time in a use or method of the invention described herein.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

A dosing study was completed to determine the maximum tolerated and feasible dose in which no adverse clinical events were observed, or in which any adverse clinical events were resolved by the subsequent dosing. The dosing study protocol is set out below.

Trypsinogen and Chymotrypsinogen A were dissolved in phosphate buffered saline (PBS) on each treatment day to give stock solutions of 1 mg/mL. Dosing solutions of the required concentrations of Trypsinogen/Chymotrypsinogen A were prepared by diluting the stock solutions together in PBS to achieve the desired final concentration of each.

For Study #1, dosing solutions of Trypsinogen/Chymotrypsinogen A at 0.0254/0.1521, 0.0381/0.2282, 0.0572/0.3423 and 0.0858/0.5135 mg/mL were prepared.

For the study, treatments were administered to animals in each group once daily for seven consecutive days in a dosing volume of 10 mL/kg. The volume of dosing solution administered to each animal was calculated and adjusted based on individual body weight measured immediately prior to dosing.

For Study #1 mice were randomised by body weight into four groups of four mice. The dosing regimen used for the study is summarised in Table 1. Trypsinogen and Chymotrypsinogen A were administered in combination as a single intravenous tail vein injection (i.v.) at doses of 10 mL/Kg. The final concentration of Trypsinogen and Chymotrypsinogen for each group were 0.254/1.521, 0.381/2.282, 0.572/3.423 and 0.858/5.135 mg/kg (Groups 1, 2, 3 and 4, respectively).

Treatment for each group in Study #1 was initiated in a staggered manner, beginning with the lowest dose of Trypsinogen/Chymotrypsinogen A, and then increasing the dose on each subsequent study day. For all data calculations and presentation, the first day of treatment for each group is designated as Study Day 0.

On the first day of each study, one mouse in Group 1 was treated with Trypsinogen/Chymotrypsinogen A at the lowest dose (0.254/1.521 mg/kg for Study #1). As there were no prolonged severe adverse effects within two hours of treatment, the remaining three mice in each of these groups were similarly treated.

As there were no prolonged severe adverse effects within 24 hours of initial treatment in Group 1 mice, one mouse in Group 2 was treated with Trypsinogen/Chymotrypsinogen A at 0.381/2.282 mg/kg for Study #1. As there were no visible signs of toxicity within two hours of this treatment, the remaining mice in each of these groups received the same treatment.

Treatment continued in this manner for the remaining two doses of Trypsinogen/Chymotrypsinogen A for Study #1 (0.572/3.423 and 0.858/5.135 mg/kg) to animals in Groups 3 and 4, respectively.

All animals in each group in each study received seven consecutive daily treatments.

| | |
|---|---|
| Mortality | Mortality checks were performed once daily in the morning during the study. |
| Clinical Observations | Animals were checked for clinical signs (such as ill health and behavioural changes) twice daily during the study. |
| Body Weights | Body weights were recorded for all animals on the first treatment day, then daily during the treatment period and for seven days following final treatment. |

Clinical Observations:

| From Distance | |
|---|---|
| Gait | Normal or Abnormal |
| Piloerection | Normal or Abnormal |
| Type of breathing | Normal or Abnormal |
| On Handling | |
| Inquisitive & alert | Normal or Abnormal |
| Body temperature | Normal or Abnormal |
| Skin Tone | Normal or Abnormal |
| Eye condition (pale, sunken) | Normal or Abnormal |
| Dehydration | Normal or Abnormal |
| Diarrhoea | Normal or Abnormal |
| Abdomen (distended/swollen) | Normal or Abnormal |
| Other signs of adverse reaction to drug or ill health | Normal or Abnormal |
| Signs previously observed, e.g. in a previous study or with other species | Normal or Abnormal |
| Skin Reddening/Irritation e.g. Radiotherapy side effects | Normal or Abnormal |
| Body condition | BC1, BC2, BC3, BC4, BC5 |

Assessment Criteria for Clinical Observations:
Gait: Limping, Paresis, Paralysis=Abnormal
Body Temperature: Warm or cold=Abnormal
Type of breathing: Rapid; Shallow or Laboured=Abnormal
Diarrhoea: Loose faeces on floor of the cage, pools of faeces on floor of the cage or running out on handling=Abnormal
Body Condition (Ref: Ullman-Cullere & Foltz. Lab. Animal Science 1999; 49:319): BC1=Animal is emaciated; BC2=Animal is underconditioned; BC3=Animal is well-conditioned; BC4=Animal is over-conditioned; BC5=Animal is obese
Clinical Observations and Adverse Events for Study #1
No adverse clinical signs were observed in any animals during the study.
Body Weight Changes
There was mean body weight gain over the course of the study (Study Days 0 to 13) for each group (2.59%, 7.48%, 7.97% and 2.03% of initial weight for animals treated with Trypsinogen and Chymotrypsinogen A at 0.254/1.521, 0.381/2.282, 0.572/3.423 and 0.858/5.135 mg/kg; Groups 1, 2, 3 and 4, respectively) (Table 2 and FIG. 1). No animals lost body weight in excess of 15% of initial weight (Table 3).

Example 2

Surprisingly, the amounts of Trypsinogen and Chymotrypsinogen A in Study #1 were well tolerated as shown from the results in Example 2 above. This was unexpected given these amounts were significantly above amounts previously used. In view of these results, a further study, Study #2, was performed using amounts of Trypsinogen and Chymotrypsinogen A, in combination, at even higher than ever previously used amounts.

For Study #2, a stock solutions of Trypsinogen and Chymotrypsinogen A were prepared at 5 and 6 mg/mL respectively. The stocks solutions were further diluted in PBS to prepare the dosing solutions of Trypsinogen/Chymotrypsinogen A for Group 1 of 0.256/1.5 mg/ml. For Groups 2 and 3, a stock solutions of Trypsinogen and Chymotrypsinogen A were prepared at 30 and 100 mg/mL respectively.

The stocks solutions were further diluted in PBS to prepare the dosing solutions of Trypsinogen/Chymotrypsinogen A for Group 2 of 8.68/50 mg/ml and for Group 3 of 4.34/25 mg/ml. It was noted that at a concentration of 50 mg/ml Chymotrypsinogen A was almost at the limit of viscosity for tail vein injection.

For Study #2 12 mice were randomised by body weight into three groups of four mice. The dosing regimen used for the study is summarised in Table 4. Trypsinogen and Chymotrypsinogen A were administered in combination as a single intravenous tail vein injection (i.v.) at doses of 10 mL/Kg. The final concentration of Trypsinogen and Chymotrypsinogen for each group were 2.6/15, 86.8/500 and 43.4/250 mg/kg (Groups 1, 2 and 3, respectively)

Treatment for each group in Study #2 was initiated in a staggered manner, beginning with the lowest dose of Trypsinogen/Chymotrypsinogen A, and then increasing the dose on each subsequent study day. For all data calculations and presentation, the first day of treatment for each group is designated as Study Day 0.

On the first day of each study, one mouse in Group 1 was treated with Trypsinogen/Chymotrypsinogen A at the lowest dose 2.6/15 mg/kg. As there were no prolonged severe adverse effects within two hours of treatment, the remaining three mice in this group were similarly treated.

As there were no prolonged severe adverse effects within 24 hours of initial treatment in Group 1 mice, one mouse in Group 2 was treated with Trypsinogen/Chymotrypsinogen A at 86.8/500 mg/kg for Study #2. As there were no visible signs of toxicity within two hours of this treatment, the remaining mice in each of these groups received the same treatment.

Treatment continued in this manner for the remaining dose of Trypsinogen/Chymotrypsinogen A for Study #2 (43.4/250 mg/kg) to animals in Group 3.
Clinical Observations and Adverse Events for Study #2
There were no adverse clinical signs observed in animals treated with Trypsinogen and Chymotrypsinogen A at 2.6/15, and 43.4/250 mg/kg; Groups 1 and 3, respectively) (Table 5).

Figure 2:
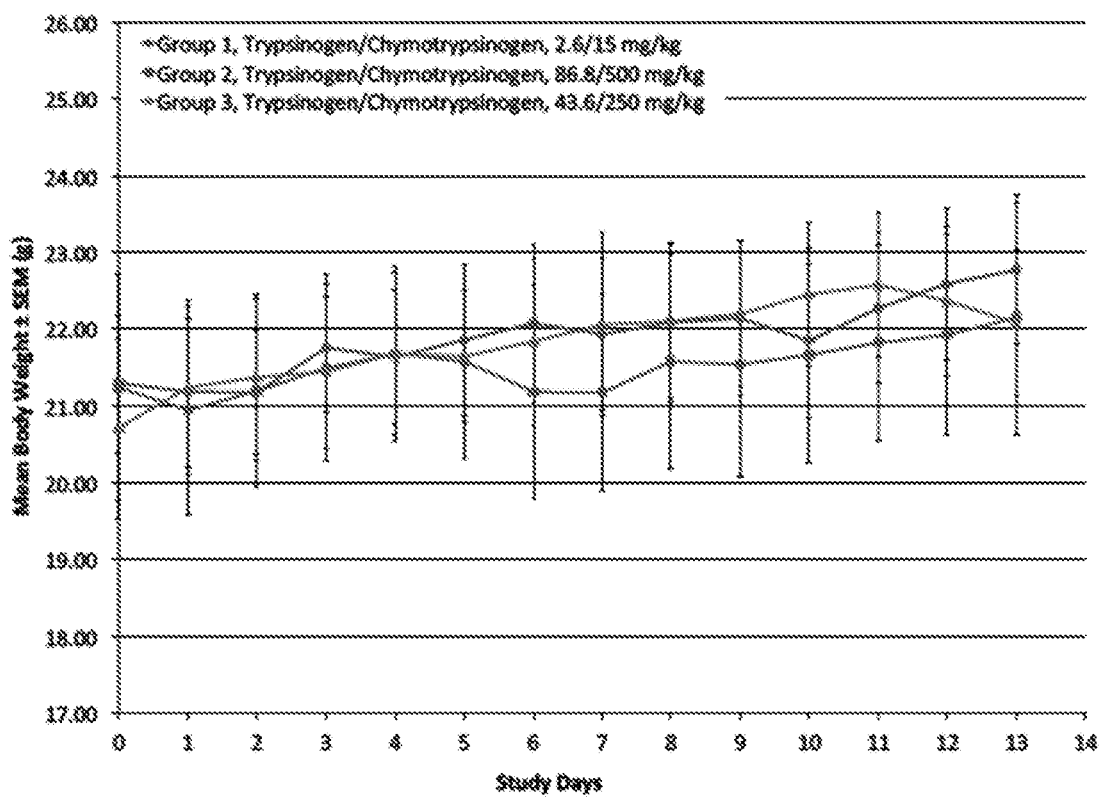
FIG. 2: Mean Body Weight±SEM (g) for Each Group During Study #2. Treatments were administered as single i.v. injection, once daily for seven consecutive days. Treatment was initiated to each group in a staggered manner, beginning with the lowest dose on the first day and then increasing the dose to Trypsinogen/Chymotrypsinogen A at 86.8/500 mg/kg on the second day. Treatment with Trypsinogen/Chymotrypsinogen A at 43.4/250 mg/kg commenced on the third day. For all data calculations and presentation, the first day of treatment for each group is designated as Study Day 0.

Reddening of the skin on the tail and temporary minor clot formations in the tail vein at the injection site were the only adverse signs observed, occurring immediately following dosing in the highest dose group (Trypsinogen/Chymotrypsinogen A at 86.8/500 mg/kg) and resolved by the time of the next dose administration (Table 5). The clinical signs did not interfere with proper dose administration.
Body Weight Changes
There was mean body weight gain over the course of the study (Study Days 0 to 13) for each group (6.98%, 4.30% and 6.61% of initial weight for animals treated with Trypsinogen and Chymotrypsinogen A at 2.6/15, 86.8/500 and 43.4/250 mg/kg; Groups 1, 2 and 3, respectively) (Table 6 and FIG. 2). No animals lost body weight in excess of 15% of initial weight (Table 7).

TABLE 1

Dosing Regimen for Study #1

| Group | Test Article | Treatment | Treatment Schedule |
|---|---|---|---|
| 1 | Trypsinogen/ Chymotrypsinogen A | 0.254/1.521 mg/kg in 10 mL/kg as a single i.v. injection | Once daily for 7 days |
| 2 | Trypsinogen/ Chymotrypsinogen A | 0.381/2.282 mg/kg in 10 mL/kg as a single i.v. injection | Once daily for 7 days |

TABLE 1-continued

Dosing Regimen for Study #1

| Group | Test Article | Treatment | Treatment Schedule |
|---|---|---|---|
| 3 | Trypsinogen/ Chymotrypsinogen A | 0.572/3.42 mg/kg in 10 mL/kg as a single i.v. injection | Once daily for 7 days |
| 4 | Trypsinogen/ Chymotrypsinogen A | 0.858/5.135 mg/kg in 10 mL/kg as a single i.v. injection | Once daily for 7 days |

Treatment was initiated to each group in a staggered manner, beginning with the lowest dose and then increasing the dose on each subsequent day.
For all data calculations and presentation, the first day of treatment for each group is designated as Study Day 0.

TABLE 2

Mean Body Weight Measurements ± SEM (g) for Each Treatment Group at Initiation and Termination of Study #1

| Group | Treatment | Body Weight Study Day 0 (mean ± SEM) | Body Weight Final Day (mean ± SEM) | Delta Body Weight (%) | Survival Number |
|---|---|---|---|---|---|
| 1 | Trypsinogen/ Chymotrypsinogen A 0.254/1.521 mg/kg | 19.86 ± 0.38 | 20.38 ± 0.43 | 2.59 | 4/4 |
| 2 | Trypsinogen/ Chymotrypsinogen A 0.381/2.282 mg/kg | 20.06 ± 0.30 | 21.56 ± 0.30 | 7.48 | 4/4 |
| 3 | Trypsinogen/ Chymotrypsinogen A 0.572/3.423 mg/kg | 20.37 ± 0.11 | 21.99 ± 0.31 | 7.97 | 4/4 |
| 4 | Trypsinogen/ Chymotrypsinogen A 0.858/5.135 mg/kg | 21.18 ± 0.40 | 21.61 ± 0.31 | 2.03 | 4/4 |

Treatments were administered as single i.v. injection, once daily for seven consecutive days.
Treatment was initiated to each group in a staggered manner, beginning with the lowest dose and then increasing the dose on each subsequent day.
For all data calculations and presentation, the first day of treatment for each group is designated as Study Day 0.

TABLE 3

Initial Body Weight and Occurrence of Lowest Body Weight (g) for Each Animal During the Course of Study #1

| Group | Treatment | Animal ID | Starting Weight (g) | Lowest Weight (g) | Days Post Initial Treatment | Delta Start to Lowest (%) |
|---|---|---|---|---|---|---|
| 1 | Trypsinogen/Chymotrypsinogen A 0.254/1.521 mg/kg | 07343 | 20.70 | 19.53 | 5 | −5.7 |
|  |  | 11414 | 19.87 | 19.70 | 12 | −0.9 |
|  |  | 37880 | 20.01 | 19.66 | 11 | −1.7 |
|  |  | 43929 | 18.87 | 18.87 | 0 | 0.0 |
| 2 | Trypsinogen/Chymotrypsinogen A 0.381/2.282 mg/kg | 07510 | 19.70 | 19.62 | 4 | −0.4 |
|  |  | 15663 | 19.88 | 19.71 | 2 | −0.9 |
|  |  | 25443 | 20.95 | 20.95 | 0 | 0.0 |
|  |  | 45040 | 19.71 | 19.65 | 2 | −0.3 |
| 3 | Trypsinogen/Chymotrypsinogen A 0.572/3.423 mg/kg | 14447 | 20.48 | 20.48 | 0 | 0.0 |
|  |  | 17670 | 20.49 | 20.49 | 0 | 0.0 |
|  |  | 25190 | 20.46 | 20.46 | 0 | 0.0 |
|  |  | 45377 | 20.05 | 20.05 | 0 | 0.0 |
| 4 | Trypsinogen/Chymotrypsinogen A 0.858/5.135 mg/kg | 08584 | 21.25 | 21.25 | 0 | 0.0 |
|  |  | 20188 | 21.82 | 21.52 | 1 | −1.4 |
|  |  | 28900 | 20.02 | 19.19 | 2 | −4.1 |
|  |  | 31187 | 21.63 | 20.80 | 2 | −3.8 |

Treatments were administered as single i.v. injection, once daily for seven consecutive days.
Treatment was initiated to each group in a staggered manner, beginning with the lowest dose and then increasing the dose on each subsequent day.
For all data calculations and presentation, the first day of treatment for each group is designated as Study Day 0.

TABLE 4

Dosing Regimen for Study #2

| Group | Test Article | Treatment | Treatment Schedule |
|---|---|---|---|
| 1 | Trypsinogen/Chymotrypsinogen A | 2.6/15 mg/kg in 10 mL/kg as a single i.v. injection | Once daily for 7 days |
| 2 | Trypsinogen/Chymotrypsinogen A | 86.8/500 mg/kg in 10 mL/kg as a single i.v. injection | Once daily for 7 days |
| 3 | Trypsinogen/Chymotrypsinogen A | 43.4/250 mg/kg in 10 mL/kg as a single i.v. injection | Once daily for 7 days |

Treatment was initiated to each group in a staggered manner, beginning with the lowest dose on the first day and then increasing the dose to Trypsinogen/Chymotrypsinogen A at 86.8/500 mg/kg on the second day.
Treatment with Trypsinogen/Chymotrypsinogen A at 43.4/250 mg/kg commenced on the third day.
For all data calculations and presentation, the first day of treatment for each group is designated as Study Day 0.

TABLE 5

Clinical Observations and Adverse Events for Study #2

| Animal ID | Observation Type | Description | Study Days Observed | Early termination |
|---|---|---|---|---|
| \multicolumn{5}{l}{Group 1: Trypsinogen/Chymotrypsinogen A 2.6/15 mg/kg} | | | | |
| 3704333 | — | — | — | — |
| 3724622 | | | | |
| 3730389 | | | | |
| 3739400 | | | | |
| \multicolumn{5}{l}{Group 2: Trypsinogen/Chymotrypsinogen A at 86.8/5005 mg/kg} | | | | |
| 3705776 | Skin and Fur | Reddened Skin on Tail | 2 to 4 | — |
|  | Clotting appearing in dosed tail vein | — | 3 | |
| 3717536 | Skin and Fur | Reddened Skin on Tail | 1 to 5 | — |
|  | Clotting appearing in dosed tail vein | — | 3 to 4 | |
| 3727819 | Skin and Fur | Reddened Skin on Tail | 1 to 5 | — |
|  | Clotting appearing in dosed tail vein | — | 3 | |
| 3733560 | Skin and Fur | Reddened Skin on Tail | 1 to 5 | — |
|  | Clotting appearing in dosed tail vein | — | 3 | |
| \multicolumn{5}{l}{Group 3: Trypsinogen/Chymotrypsinogen A 43.4/250 mg/kg} | | | | |
| 3714640 | — | — | — | — |
| 3716014 | | | | |
| 3734449 | | | | |
| 3746801 | | | | |

Treatment was initiated to each group in a staggered manner, beginning with the lowest dose on the first day and then increasing the dose to Trypsinogen/Chymotrypsinogen A at 86.8/500 mg/kg on the second day.
Treatment with Trypsinogen/Chymotrypsinogen A at 43.4/250 mg/kg commenced on the third day.
For all data calculations and presentation, the first day of treatment for each group is designated as Study Day 0.

TABLE 6

Mean Body Weight Measurements ± SEM (g) for Each Treatment Group at Initiation and Termination of Study #2

| Group | Treatment | Body Weight Study Day 0 (mean ± SEM) | Body Weight Final Day (mean ± SEM) | Delta Body Weight (%) | Survival Number |
|---|---|---|---|---|---|
| 1 | Trypsinogen/Chymotrypsinogen A 2.6/15 mg/kg | 21.29 ± 0.89 | 22.77 ± 0.97 | 6.98 | 4/4 |
| 2 | Trypsinogen/Chymotrypsinogen A 86.8/500 mg/kg | 21.23 ± 1.48 | 22.14 ± 1.52 | 4.30 | 4/4 |
| 3 | Trypsinogen/Chymotrypsinogen A 43.4/250 mg/kg | 20.70 ± 1.18 | 22.07 ± 0.95 | 6.61 | 4/4 |

Treatments were administered as single i.v. injection, once daily for seven consecutive days.
Treatment was initiated to each group in a staggered manner, beginning with the lowest dose on the first day and then increasing the dose to Trypsinogen/Chymotrypsinogen A at 86.8/500 mg/kg on the second day.
Treatment with Trypsinogen/Chymotrypsinogen A at 43.4/250 mg/kg commenced on the third day.
For all data calculations and presentation, the first day of treatment for each group is designated as Study Day 0.

TABLE 7

Initial Body Weight and Occurrence of Lowest Body Weight (g) for Each Animal During the Course of Study #2

| Group | Treatment | Animal ID | Starting Weight (g) | Lowest Weight (g) | Days Post Initial Treatment | Delta Start to Lowest (%) |
|---|---|---|---|---|---|---|
| 1 | Trypsinogen/Chymotrypsinogen A 2.6/15 mg/kg | 04333 | 20.89 | 20.21 | 1 | −3.3 |
|  |  | 24622 | 23.82 | 23.19 | 2 | −2.6 |
|  |  | 30389 | 19.64 | 19.40 | 2 | −1.2 |
|  |  | 39400 | 20.79 | 20.50 | 2 | −1.4 |
| 2 | Trypsinogen/Chymotrypsinogen A 86.8/500 mg/kg | 05776 | 18.85 | 18.73 | 1 | −0.6 |
|  |  | 17536 | 20.76 | 20.35 | 2 | −2.0 |
|  |  | 27819 | 25.50 | 24.83 | 2 and 7 | −2.6 |
|  |  | 33560 | 19.81 | 19.57 | 6 | −1.2 |
| 3 | Trypsinogen/Chymotrypsinogen A 43.6/250 mg/kg | 14640 | 19.38 | 19.38 | 0 | 0.0 |
|  |  | 16014 | 20.08 | 20.08 | 0 | 0.0 |
|  |  | 34449 | 19.15 | 19.15 | 0 | 0.0 |
|  |  | 46801 | 24.20 | 24.18 | 5 | −0.1 |

Treatment were administered as single i.v. injection, once daily for seven consecutive days.
Treatment was initiated to each group in a staggered manner, beginning with the lowest dose on the first day and then increasing the dose to Trypsinogen/Chymotrypsinogen A at 86.8/500 mg/kg on the second day. Treatment with Trypsinogen/Chymotrypsinogen A at 43.4/250 mg/kg commenced on the third day. For all data calculations and presentation, the first day of treatment for each group is designated as Study Day 0.

Example 3

The study was performed to assess anti-tumour efficacy of Trypsinogen and Chymotrypsinogen A, administered in combination against Pan02 mouse pancreatic cancer cells, orthotopically inoculated in female C57BL/6 mice.

Cell Line

Pan02 mouse pancreatic tumour cells were sourced from National Cancer Institute (Frederick, MD, USA).

Tumour Cell Culture

Pan02 mouse pancreatic tumour cells (working stock VP-Stock 1235) were cultured in RPMI 1640 cell culture medium supplemented with 10% FBS, 1% GlutaMAX™ and 1% penicillin-streptomycin, and grown at 37° C. in a humidified cell culture incubator supplied with 5% $CO_2$. The cells were harvested (Passage 7) by trypsinisation, washed twice in HBSS and counted (using trypan blue exclusion). The final cell density was adjusted with HBSS:Matrigel™ (1:1, v/v) to $5\times10^7$ Pan02 cells/mL.

The use of Matrigel™ in the inoculation suspension is known to support early vascularisation which can increase the take-rate of tumours, and therefore has the potential to decrease tumour size variability.

Tumour Cell Inoculation

Forty C57BL/6 female mice were inoculated while under intraperitoneally injected anaesthesia (Ketamine (14 mg/mL)/Xylazine (0.9 mg/mL)). Prior to inoculation, the skin at the incision site was swabbed with topical povidone iodine solution and then alcohol. An incision was made to expose the pancreas. A needle was introduced directly into the pancreas tail where 20 µL of cell suspension, consisting of $1\times10^6$ Pan02 cells, was discharged.

Mice were administered a 200 µL bolus dose of Buprenex (Buprenorphine HCl, 0.01 mg/mL) subcutaneously for pain relief at the time of surgery and the following day.

Tumour Take-Rate Determination

Ten randomly selected animals (Group 0) were euthanised seven days post inoculation to assess the size and take rate of tumours in the pancreas. The pancreas was excised and examined for the presence of a tumour.

The presence of a tumour was confirmed in the pancreas of all 10 of these animals.

Randomisation

Two days following confirmation of successful tumour take-rate, 30 of the remaining animals were randomised, based on body weight, into three groups of 10 (nine days post-inoculation; Study Day 0).

Compound Formulation

Trypsinogen and Chymotrypsinogen A were dissolved in phosphate buffered saline (PBS) on each treatment day to give stock solutions of 1 mg/mL. The dosing solutions of Trypsinogen/Chymotrypsinogen A at 2.75/16.5 and 8.33/50 mg/mL (ratio of 1:6) were prepared by diluting the Trypsinogen solution first in PBS and then adding Chymotrypsinogen A.

Compound Administration

The dosing regimen used in this study is summarised in Table 8.

The animals assigned for take-rate assessment (Group 0) remained untreated.

Vehicle Control (PBS; Groups 1) and Trypsinogen/Chymotrypsinogen A (in combination in a single injection) at doses of 27.5/165 (Group 2) and 83.3/500 mg/kg (Groups 3) were administered once daily i.v. in a dosing volume of 10 mL/kg. The volume of dosing solution administered to each animal was calculated and adjusted based on individual body weight measured immediately prior to dosing.

Treatments commenced on Study Day 0 (nine-days post-inoculation). Treatments were administered to animals in Groups 1, 2 and 3 for 26 consecutive days.

Termination Procedure

All take-rate assessment animals and those in Groups 1, 2 and 3 were euthanised via carbon dioxide inhalation by approved standard procedures.

Sample Collection

Figure 4:
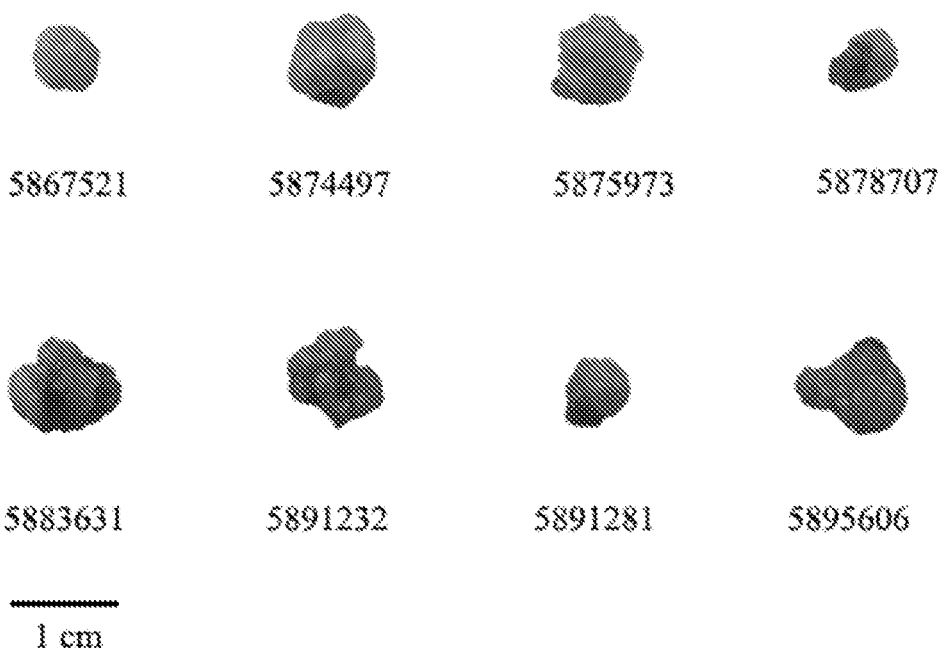
FIG. 4: Images of excised tumours from mice in Group 1 (PBS, 10 ml/kg, daily i.v) Day 26 in study described in Example 3 performed to assess anti-tumour efficacy of Trypsinogen and Chymotrypsinogen A, administered in combination against Pan02 mouse pancreatic cancer cells, orthotopically inoculated in female C57BL/6 mice.
Figure 6:
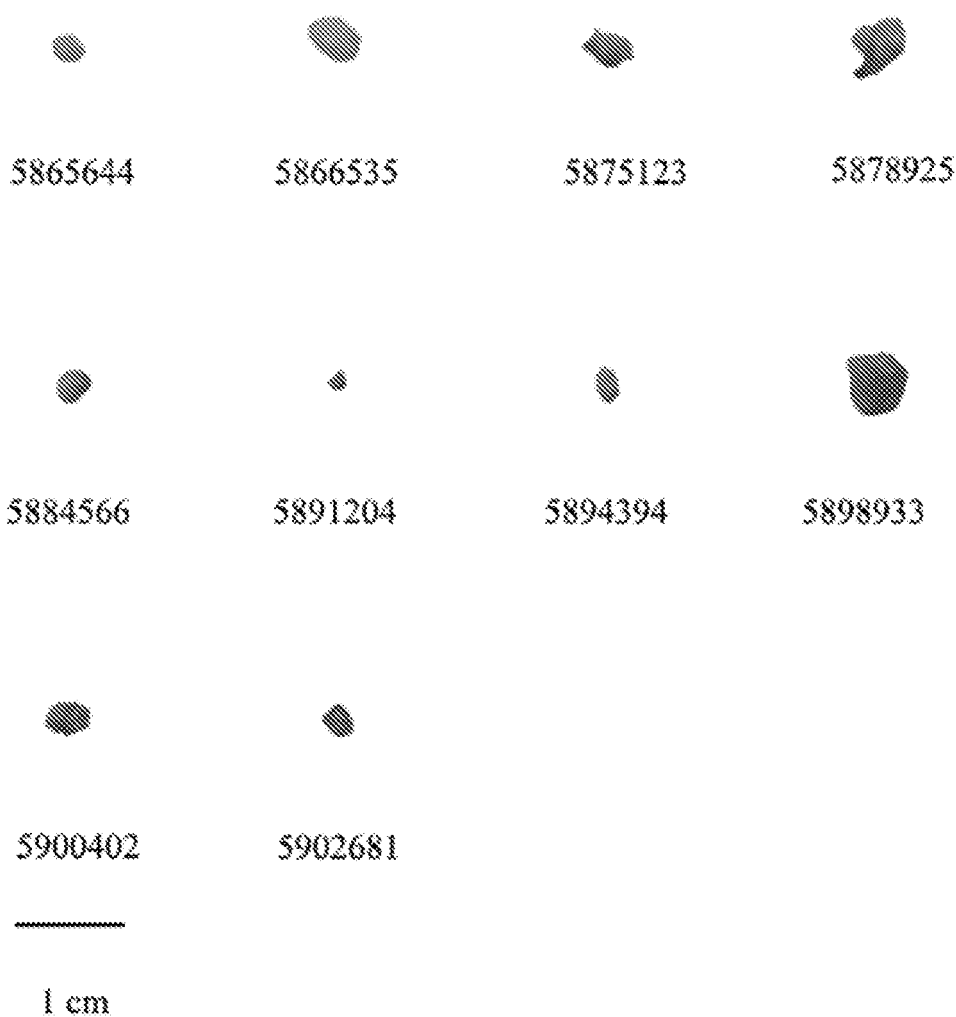
FIG. 6: Images of excised tumours from mice in Group 3 (T:C, 83.3 mg/kg:500 mg/kg) Day 26 in study described in Example 3 performed to assess anti-tumour efficacy of Trypsinogen and Chymotrypsinogen A, administered in combination against Pan02 mouse pancreatic cancer cells, orthotopically inoculated in female C57BL/6 mice.

Upon termination, the pancreas was excised from all animals with tumour intact. The tumour was isolated from the pancreas tissue, weighed and then photographed (FIGS. 4 to 6). A 25 mg portion of tumour from each of the samples in Groups 4 and 5 were stored at −80° C. and shipped to Adaptive Biotechnologies Corp. for further analysis.

Calculations

Mean percentage change in body weight (% BW Change) between Day 0 and any given day (Day X) was calculated using the equation:

$$\% \text{ BW Change} = \text{mean}(BW_{Study\ Day\ X})/\text{mean}(BW_{Study\ Day\ 0}) \times 100\% - 100\%$$

where $BW_{Study\ Day\ 0}$=initial value on Day 0 and $BW_{Study\ Day\ X}$=current value on Day X.

Percentage change in mean tumour weight for treated groups relative to the control group was calculated using the following equation:

$$\text{Percentage change} = ((\text{Mean}_{Control} - \text{Mean}_{Treatment})/\text{Mean}_{Control}) \times 100$$

Statistical Calculations

All statistical calculations were performed using Prism 6 for Mac OS X (GraphPad Software Inc, La Jolla, CA, USA).

Normality of all data-sets was tested using the Kolmogorov-Smirnov (KS) normality test.

A paired t-test was used to determine if body weight changed significantly within a treatment group between Study Day 0 and the termination day of each group.

Comparison of tumour weight at termination of the study was made between Groups 1, 2 and 3 using One-Way Analysis of Variance (ANOVA). Significant differences between groups were determined using Holm-Sidak's Multiple Comparisons Test.

A p value of ≤0.05 was considered significant.

Results and Observations

Body Weight Changes

There was a small (not significant) mean body weight loss (0.54% of initial weight) in animals treated with Vehicle Control for 26 days (PBS; Group 1).

All other groups showed mean body weight gain; 0.82% and 2.72% of initial weight for groups treated with Trypsinogen/Chymotrypsinogen A at 27.5/165 and 83.3/500 mg/kg for 26 days (Groups 2 and 3, respectively).

Efficacy of Compounds

There was significant (p≤0.05) reduction in mean tumour weight in animals treated for 26 days with Trypsinogen/Chymotrypsinogen A at 83.3/500 mg/kg (30.2 mg; 85.9% inhibition; Group 3) compared with Vehicle Control (PBS; 214.8 mg; Group 1), but not between Trypsinogen/Chymotrypsinogen A at 27.5/165 mg/kg (196.5 mg; 8.5% inhibition; Group 2) and the Vehicle Control (Table 9 and FIG. 3).

Conclusion

Anti-tumour efficacy of daily treatment with Trypsinogen and Chymotrypsinogen A, administered in combination as a single intravenous injection at doses of 27.5/165 or 83.3/500 mg/kg, was assessed against Pan02 mouse pancreatic cancer cells, orthotopically inoculated in female C57BL/6 mice.

Measurements of tumour weight at termination showed significant (p≤0.05) anti-tumour efficacy in animals treated with high-dose Trypsinogen/Chymotrypsinogen A compared with control-treated animals after 26 days of treatment in this study.

TABLE 8

| Dosing Regimen | | | | |
|---|---|---|---|---|
| Group | Number of Animals | Test Article | Treatment | Treatment Schedule |
| 0 | 10 | No treatment (for take-rate assessment) | — | — |
| 1 | 10 | Vehicle Control (PBS) | 10 mL/kg, i.v. | Once daily (Study Days 0 to 25) |
| 2 | 10 | Trypsinogen/ Chymotrypsinogen A | 27.5/165 mg/ kg in 10 mL/ kg as a single i.v. injection | Once daily (Study Days 0 to 25) |
| 3 | 10 | Trypsinogen/ Chymotrypsinogen A | 83.3/500 mg/ kg in 10 mL/ kg as a single i.v. injection | Once daily (Study Days 0 to 25) |

TABLE 9

Mean Tumour Weight ± SEM at Termination (mg) for Each Group

| Group | Treatment | Termination Day | Number of Animals | Mean Tumour Weight ± SEM (mg) | % Tumour inhibition* |
|---|---|---|---|---|---|
| 1 | Vehicle Control (PBS) | 26 | 8 | 214.8 ± 23.4 | N/A |
| 2 | Trypsinogen/ Chymotrypsinogen A 27.5/165 mg/kg | 26 | 9 | 196.5 ± 30.5 | 8.5 |
| 3 | Trypsinogen/ Chymotrypsinogen A 83.3/500 mg/kg | 26 | 10 | 30.2 ± 8.2$^{a,b}$ | 85.9 |

Treatments were administered as a single i.v. injection, once daily (Study Days 0 to 25 for Groups 1, 2 and 3. Groups 1, 2 and 3 were terminated on Study Day 26. Tumours were not collected from animals that were found dead (one each in Groups 1 and 2). The value for one animal in Group 1 that was euthanised on Study Day 6 was not included in the analyses.

$^a$p ≤ .05 compared with Group 1 (p < 0.05; Holm-Sidak's Multiple Comparisons Test).

$^b$p ≤ 0.05 compared with Group 2 (p < 0.05; Holm-Sidak's Multiple Comparisons Test).

Figure 3:
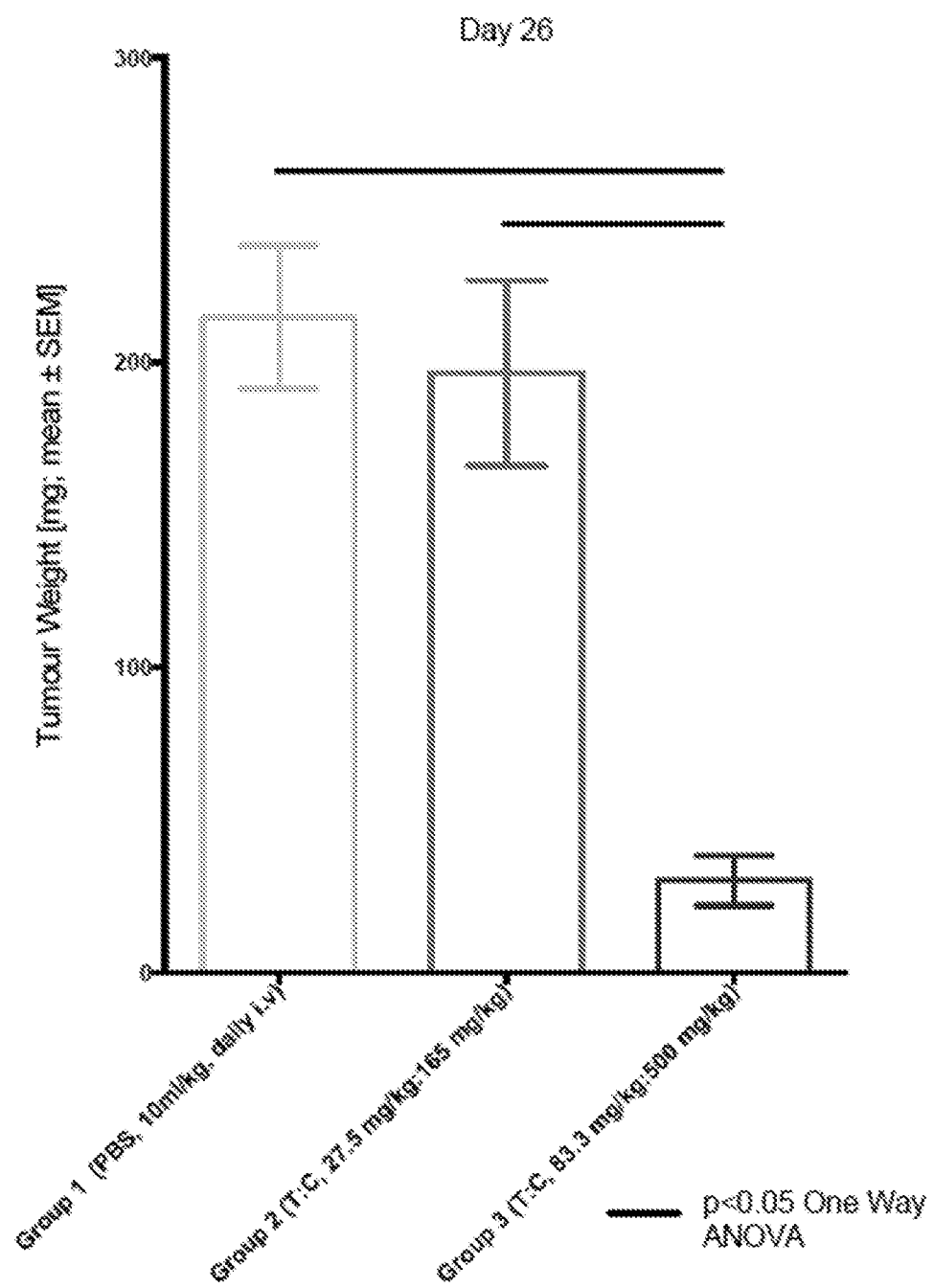
FIG. 3: Results of mean tumour weight±SEM (mg) of PBS control mice (Group 1, n=8) and mice receiving T:C, 27.5 mg/kg:165 mg/kg (Group 2, n=9) or T:C, 83.3 mg/kg:500 mg/kg (Group 3, n=10) in study described in Example 3 performed to assess anti-tumour efficacy of Trypsinogen and Chymotrypsinogen A, administered in combination against Pan02 mouse pancreatic cancer cells, orthotopically inoculated in female C57BL/6 mice. Treatments were administered as single i.v. injection, once daily on Study Days 0 to 25. Animals were terminated on Study Day 26.

Mean tumour weight ± SEM for each group are depicted in FIG. 3.

*% Tumour inhibition was calculated for Groups 2 and 3 using Group 1 as the control.

N/A: not applicable

Example 4

The study was performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice.

Cell Line

A2780 human ovarian carcinoma cells were sourced from National Cancer Institute (Frederick, MD, USA).

Tumour Cell Culture

A2780 human ovarian cancer cells (working stock VP-Stock 1277) were cultured in DMEM supplemented with 10% FBS, 1% GlutaMAX™ and 1% penicillin-streptomycin, and grown at 37° C. in a humidified cell culture incubator supplied with 5% $CO_2$. The cells were harvested (Passage 8) by trypsinisation, washed twice in HBSS and counted (using trypan blue exclusion). The final cell density was adjusted with HBSS:Matrigel™ (1:1, v/v) to $2.0 \times 10^8$ cells/mL.

The use of Matrigel™ in the inoculation suspension is known to support early vascularisation which can increase the take-rate of tumours, and therefore has the potential to decrease tumour size variability.

Tumour Cell Inoculation

Sixty athymic Nude-Foxn1$^{nu}$ mice were inoculated while under intraperitoneally injected anaesthesia (Ketamine (14 mg/mL)/Xylazine (0.9 mg/mL)). Prior to inoculation, the skin at the incision site was swabbed with alcohol. An incision was made to expose the ovary. A needle was introduced directly into the ovary where 5 μL of cell suspension, consisting of $1 \times 10^6$ A2780 cells was discharged.

Mice were administered a 200 μL bolus dose of Buprenex (Buprenorphine HCl, 0.01 mg/mL) subcutaneously for pain relief at the time of surgery and the following day.

Randomisation

The animals were randomised, based on body weight, into five groups of 12 and one group of 24, 7 days post-inoculation (Study Day 0).

Compound Formulation

Trypsinogen and Chymotrypsinogen A were dissolved in phosphate buffered saline (PBS) on each treatment day to give stock solutions of 30 and 100 mg/mL, respectively. Dosing solution of Trypsinogen/Chymotrypsinogen A at 8.33/50, 2.75/16.5 and 0.91/5.4 mg/mL (ratio of 1:6) were prepared by diluting Trypsinogen solution first in PBS and then adding Chymotrypsinogen A.

Compound Administration

The dosing regimen used in this study is summarised in Table 10.

Animals in Group 1 remained untreated for tumour take-rate assessment.

Vehicle Control (PBS; Group 2) and Trypsinogen and Chymotrypsinogen A at doses of 83.3/500, 27.5/165 and 9.1/54 mg/kg (Groups 3, 4 and 5, respectively; in combination in a single injection) were administered once daily via intravenous (i.v.) tail vein injection in a dosing volume of 10 mL/kg (12 animals per group). The volume of dosing solution administered to each animal was calculated and adjusted based on individual body weight measured immediately prior to dosing. Treatments commenced on Study Day 0 and were administered for 21 consecutive days.

Tumour Take-Rate Determination

The untreated animals in Group 1 were euthanised seven days after the onset of treatment (14 days post-inoculation) to assess the size and take rate of tumours in the ovary.

The presence of a tumour was confirmed in the ovary of all 12 animals, then the tumour was isolated from the excised ovary and weighed for all animals. Tumour photographic images are presented in FIGS. 8 to 11.

Termination Procedure

All animals were euthanised via carbon dioxide inhalation by approved standard procedures (Groups 1 through 5).

Sample Collection

Upon termination, the ovary was excised from all animals with tumour intact. The tumour was isolated from the ovarian tissue and weighed. Tumours from animals receiving 21 days of treatment (Groups 2 through 5) were also photographed.

Calculations

Mean percentage change in body weight (% BW Change) between Day 0 and any given day (Day X) was calculated using the equation:

$$\% \text{ BW Change} = \text{mean}(BW_{Study\ Day\ X})/\text{mean}(BW_{Study\ Day\ 0}) \times 100\% - 100\%$$

where $BW_{Study\ Day\ 0}$=initial value on Day 0 and $BW_{Study\ Day\ X}$=current value on Day X.

Percentage inhibition of tumour growth for treated groups relative to the control group was calculated using the following equation:

$$\text{Percentage inhibition} = ((\text{Mean}_{Control} - \text{Mean}_{Treatment})/\text{Mean}_{Control}) \times 100$$

Statistical Calculations

All statistical calculations were performed using Prism 6 for Mac OS X (GraphPad Software Inc, La Jolla, CA, USA).

Normality of all data-sets was tested using the D'Agostino and Pearson omnibus normality test.

A paired t-test was used to determine if body weight changed significantly within groups receiving 21 days of treatment (Groups 2 through 5) between Study Day 0 and termination of the study. Where the data was not normally distributed, significance was determined using the Wilcoxon Matched Pairs Signed Rank Test.

Comparison of tumour weight at termination of the study was made between groups receiving 21 days of treatment (Groups 2 through 5) using One-Way Analysis of Variance (ANOVA).

A p value of ≤0.05 was considered significant.

Results and Observations

Body Weight Changes

There was significant (p≤0.05) mean body weight gain between Study Days 0 and 7 in untreated animals (4.33% of initial weight; Group 1).

There was mean body weight gain between Study Days 0 and 21 in the groups treated for 21 days with Vehicle Control (PBS; 6.56% of initial weight; Group 2) and all doses of Trypsinogen/Chymotrypsinogen A (83.3/500, 27.5/165 and 9.1/54 mg/kg; 8.60%, 6.00% and 3.89% of initial weight; Groups 3, 4 and 5, respectively). Body weight gain was significant (p≤0.05) in all groups except low-dose treatment (Group 5).

Efficacy of Compounds

There was significant (p≤0.05) reduction in mean tumour weight in animals treated for 21 days with mid- and low-dose Trypsinogen/Chymotrypsinogen A (27.5/165 and 9.1/54 mg/kg; 957.3 and 1074.2 mg; 53.6% and 47.9%; Groups 4 and 5, respectively) compared with Vehicle Control (PBS; 2062.2 mg; Group 2), but not high-dose Trypsinogen/Chymotrypsinogen A (83.3/500 mg/kg; 1762.2 mg; 14.5%; Group 3) (Table 11 and FIG. 7).

Tumour weights for untreated animals (Group 1) euthanised on Day 7 for take-rate assessment were not included in the analysis.

Conclusion

Anti-tumour efficacy of daily treatment with Trypsinogen and Chymotrypsinogen A, administered in combination as a single intravenous injection at doses of 83.3/500, 27.5/165 or 9.1/54 mg/kg, was assessed against A2780 human ovarian cancer cells, orthotopically inoculated in female athymic nude-Foxn1$^{nu}$ mice.

Measurements of tumour weight at termination showed significant (p≤0.05) anti-tumour efficacy in animals treated with mid- and low-dose Trypsinogen/Chymotrypsinogen A compared with Vehicle control-treated animals after 21 days of treatment in this study. Significant anti-tumour efficacy was not observed following high-dose treatment.

TABLE 10

Dosing Regimen

| Group | Test Article | Treatment | Treatment Schedule |
|---|---|---|---|
| 1 | No treatment (take-rate assessment) | — | — |
| 2 | Vehicle Control (PBS) | 10 mL/kg, i.v. | once daily (Study Days 0 to 20) |
| 3 | Trypsinogen/ Chymotrypsinogen A | 83.3/500 mg/kg in 10 mL/kg as a single i.v. injection | once daily (Study Days 0 to 20) |
| 4 | Trypsinogen/ Chymotrypsinogen A | 27.5/165 mg/kg in 10 mL/kg as a single i.v. injection | once daily (Study Days 0 to 20) |
| 5 | Trypsinogen/ Chymotrypsinogen A | 9/54 mg/kg in 10 mL/kg as a single i.v. injection | once daily (Study Days 0 to 20) |
| 6 | Trypsinogen/ Chymotrypsinogen A | 83.3/500 mg/kg in 10 mL/kg as a single i.v. injection | once on Study Day 19 |

TABLE 11

Mean Tumour Weight ± SEM at Termination (mg) for Each Group

| Group Treatment | Number of Animals | Termination Day | Mean Tumour Weight ± SEM (mg) | % Tumour inhibition |
|---|---|---|---|---|
| 1 No treatment (take-rate assessment) | 12 | 7 | 33.0 ± 9.0 | N/A |
| 2 Vehicle Control (PBS) | 12 | 21 | 2062.2 ± 331.4 | N/A |
| 3 Trypsinogen/ Chymotrypsinogen A 83.3/500 mg/kg | 12 | 21 | 1762.2 ± 142.4 | 14.5 |
| 4 Trypsinogen/ Chymotrypsinogen A 27.5/165 mg/kg | 12 | 21 | 957.3 ± 232.9$^a$ | 53.6 |
| 5 Trypsinogen/ Chymotrypsinogen A 9.1/54 mg/kg | 12 | 21 | 1074.2 ± 225.5$^a$ | 47.9 |

Figure 7:
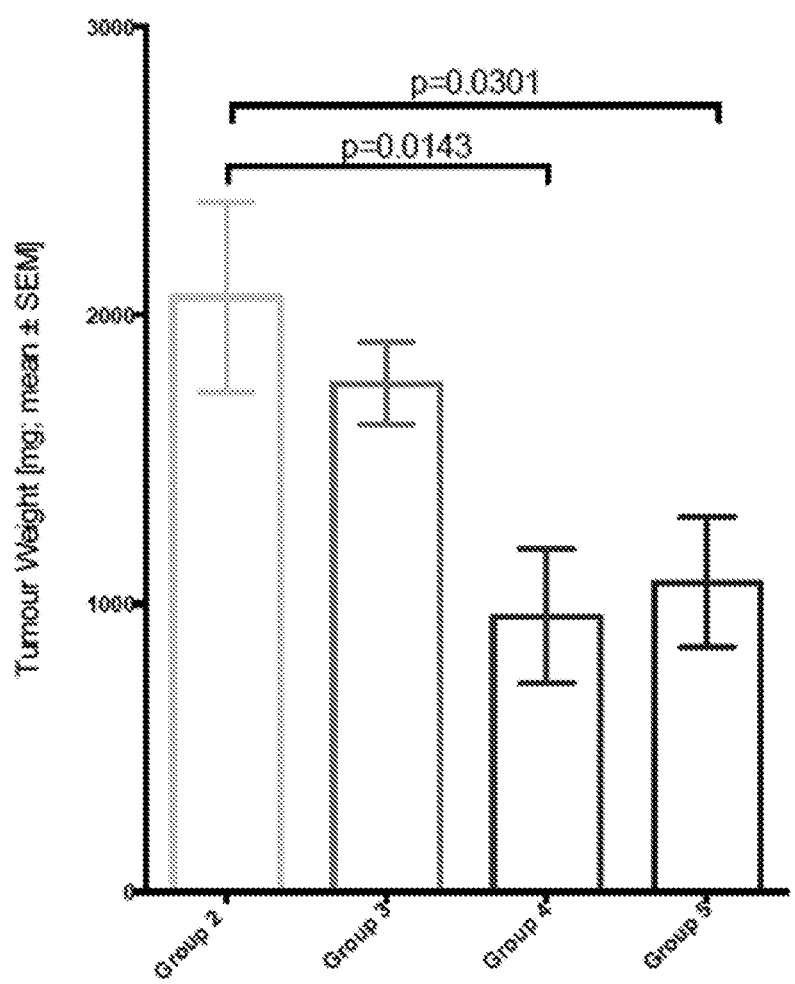
FIG. 7: Mean Tumour Weight±SEM (g) in Group 2: Vehicle Control (PBS). Group 3: Trypsinogen/Chymotrypsinogen A, 83.3/500 mg/kg. Group 4: Trypsinogen/Chymotrypsinogen A, 27.5/165 mg/kg. Group 5: Trypsinogen/Chymotrypsinogen A, 9.1/54 mg/kg, in study described in Example 4 performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice. Treatments were administered as a single i.v. injection, once daily (Study Days 0 to 20). These animals were terminated on Study Day 21.
Figure 10:
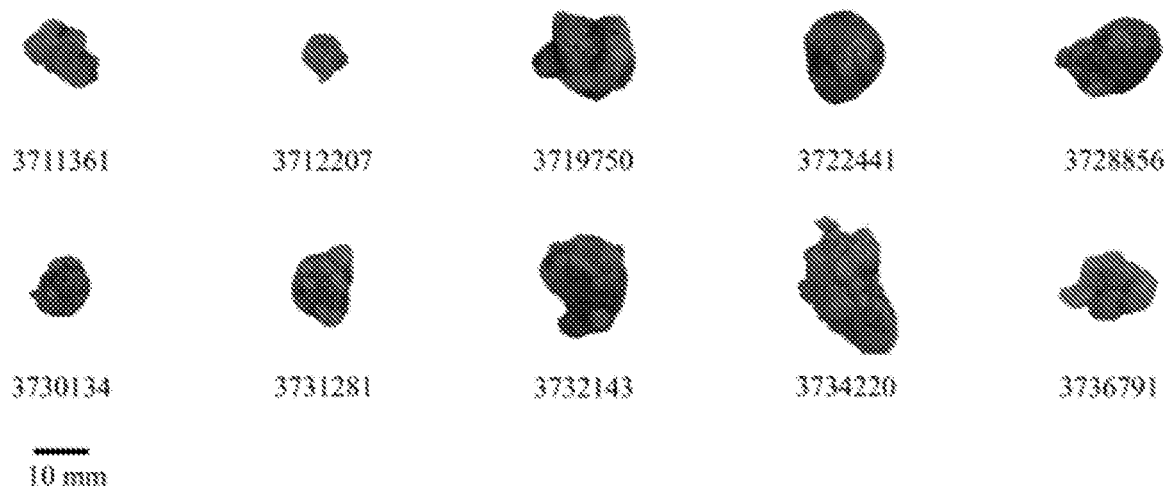
FIG. 10: Images of excised tumours at study termination for Group 4: Trypsinogen/Chymotrypsinogen A, 27.5/165 mg/kg in study described in Example 4 performed to assess anti-tumour efficacy of Trypsinogen and Chymotrypsinogen A, administered in combination, against A2780 human ovarian cancer cells orthotopically inoculated in female Athymic Nude-Foxn1$^{nu}$ mice.

Untreated animals in Group 1 were euthanized on Study Day 7 (14 days post-inoculation) for tumour take-rate assessment. Tumour weights for animals in Group 1 were not included in the statistical analysis.
Treatments were administered to animals in Groups 2 through 5 as a single i.v. injection, once daily (Study Days 0 to 20). These animals were terminated on Study Day 21.
$^a$p ≤ 0.05 compared with Group 2 (Holm-Sidak's Multiple Comparisons Test).
Mean tumour weight ± SEM for each group is depicted in FIG. 7.
N/A: not applicable Example 5

Human dose conversion can be by any of the relevant methods described in U.S. Department of Health and Human Services Food and Drug Administration Center for Drug Evaluation and Research (CDER), Estimating the Maximum Safe Starting Dose in Initial Clinical Trials for Therapeutics in Adult Healthy Volunteers. Rockville, MD 2005, incorporated herein by reference.

For example, the Human Equivalent Dose from a dose that has been administered to a mouse can be determined as follows:

Human Equivalent Dose (HED in mg/kg)=Animal Dose (mg/kg)×Animal K÷Human K, where K is a correction factor reflecting the relationship between body weight and body surface area.

For a typical adult (body weight 60 kg, body surface area 1.6 m$^2$), K is 37 and mouse K is 3. For example, 500 mg/kg amount described herein can be converted to about 41 mg/kg for an equivalent human dose, and other exemplary conversions using this formula include:

Chymotrypsinogen:
Mouse (mg/kg): 1.5, 2, 3.5, 5, 15, 45, 135, 250 and 500.
Human (mg/kg): 0.12, 0.16, 0.28, 0.4, 1.2, 3.6, 11, 20 and 41

Trypsinogen:
Mouse (mg/kg): 0.25, 0.4, 0.6, 0.8, 2.5, 8, 20, 40 and 80.
Human (mg/kg): 0.02, 0.03, 0.05, 0.065, 0.2, 0.65, 1.6, 3.2 and 6.5.

Chymotrypsinogen:
Mouse (mg/kg): 15, 54 165, 250, 500.
Human (mg/kg): 1.2, 4.4, 13, 20 and 41.

Trypsinogen:
Mouse (mg/kg): 2.6, 9, 27.5, 43.4, 83.3, 86.8.
Human (mg/kg): 0.2, 0.7, 2.2, 3.5, 6.75 and 7.

The present invention includes human conversions for all amounts in mg/kg referred to herein, including Tables 1, 4, 8 and 10 and anywhere else in this document, based on human body weights of 50, 60, 70, 80, 90, 100 or more kg and body surface area of 1.1, 1.2, 1.3, 1.4, 1.5, 1.6, 1.7, 1.8 or more m$^2$.

The human equivalent doses described herein are derived using the methods described in the CDER 'Estimating the Maximum Safe Starting Dose in Initial Clinical Trials for Therapeutics in Adult Healthy Volunteers' for dose conversion based on body surface area. It will be appreciated that any variation on the methods described in the CDER document may also be utilised for determining an appropriate human dose from the dosages administered to mice, as described herein (for example, in some circumstances it may be appropriate to dose scaling based on body weight rather than on body surface area). Moreover, the skilled person will also be familiar with methods for determining the appropriate dose for a juvenile human (i.e., non-adult human), as well as methods for determining the appropriate dose in a non-human organism, to which the methods of the present invention may be applied. The skilled person will also be familiar with methods for adjusting the appropriate dose depending on the intended method of administration (for example, intravenous, intramuscular, subcutaneous, topical, oral or other method of administration).

Example 6

The following experiments were performed to examine ratios of chymotrypsinogen to trypsinogen greater than 8:1.

Materials and Methods

Materials

| Material | Supplier |
|---|---|
| Dulbecco's Modified Eagle Medium (DMEM), Eagle's Minimum Essential Medium (EMEM), Minimum Essential Medium (MEM), Roswell Park Memorial Institute (RPMI) 1640 cell culture medium, Foetal Bovine Serum (FBS), GlutaMAX ™, sodium bicarbonate, penicillinstreptomycin (Pen/Strep) and trypsin | Invitrogen USA (Carlsbad, CA, USA) |
| CellTiter-Blue ® Cell Viability Assay | Promega (Madison, WI, USA) |
| Trypan Blue | Sigma-Aldrich (St Louis, MO, USA) |

Cell Culture

The following table (Table 12) shows the growth conditions and initial cell seeding densities in cells per well used in all $IC_{50}$ determination and combination assays. The cells were cultured at 37° C. in a humidified cell culture incubator supplied with 95% air/5% $CO_2$.

The C8161.9 cell line was sourced from Dr. Gavin Robertson's Laboratory (College of Medicine, Pennsylvania State University, Hershey, PA, USA)).

The HuH-7 cell line was sourced from the Japanese Collection of Research Bioresources (JCRB) Cell Bank (Osaka, Japan).

The SNB-19 cell line was sourced from the Deutsche Sammlung von Mikroorganismen und Zellkulturen (DSMZ) (German Collection of Microorganisms and Cell Cultures) (Braunschweig, Germany).

All cell lines were utilized in assays up to passage 10.

Test Articles

| Test Article 1 | |
|---|---|
| Identity: | Trypsinogen |
| Description: | White powder |
| Lot Number: | 0F001644 |
| Storage Conditions: | −20° C. |
| Handling Precautions: | Standard laboratory precautions |
| Manufacturer/Supplier: | Applichem (Darmstadt, Germany)/ Enzyme Supplies (Oxford, UK) |

| Test Article 2 | |
|---|---|
| Identity: | Chymotrypsinogen |
| Description: | White powder |
| Lot Number: | 3J006510 |
| Storage Conditions: | −20° C. |
| Handling Precautions: | Standard laboratory precautions |
| Manufacturer/Supplier: | Applichem (Darmstadt, Germany)/ Enzyme Supplies (Oxford, UK) |

| Cell line | Tumour Type | Cell culture medium | Seeding Density |
|---|---|---|---|
| 786-O | Kidney | RPMI + 10% FBS + 1% GlutaMAX ™ + 1% Pen/Strep | 400 |
| A2780 | Ovary | DMEM + 10% FBS + 1% GlutaMAX ™ + 1% Pen/Strep | 2500 |
| ACHN | Kidney | MEM + 10% FBS + 1% GlutaMAX ™ + 1% Pen/Strep | 4000 |
| BT-474 | Breast | RPMI + 10% FBS + 1% GlutaMAX ™ + 1% Pen/Strep + 1% $NaHCO_3$ | 10000 |
| C8161.9 | Melanoma | DMEM + 10% FBS + 1% GlutaMAX ™ + 1% Pen/Strep | 1500 |
| DAOY | Brain | RPMI + 10% FBS + 1% GlutaMAX ™ + 1% Pen/Strep | 1500 |
| DU 145 | Prostate | RPMI + 10% FBS + 1% GlutaMAX ™ + 1% Pen/Strep | 800 |
| G-361 | Melanoma | RPMI + 10% FBS + 1% GlutaMAX ™ + 1% Pen/Strep | 3000 |
| HCT 116 | Colorectal | RPMI + 10% FBS + 1% GlutaMAX ™ + 1% Pen/Strep | 1500 |
| HCT-15 | Colorectal | RPMI + 10% FBS + 1% GlutaMAX ™ + 1% Pen/Strep | 1500 |
| Hep3B2.1-7 | Liver | RPMI + 10% FBS + 1% GlutaMAX ™ + 1% Pen/Strep | 1500 |
| HL-60 | Leukaemia | RPMI + 10% FBS + 1% GlutaMAX ™ + 1% Pen/Strep | 50000 |
| HT-1080 | Fibrosarcoma | EMEM + 10% FBS + 1% GlutaMAX ™ + 1% Pen/Strep | 1500 |
| HT-29 | Colorectal | RPMI + 10% FBS + 1% GlutaMAX ™ + 1% Pen/Strep | 4000 |
| HuH-7 | Liver | DMEM + 10% FBS + 1% GlutaMAX ™ + 1% Pen/Strep | 4000 |
| MCF-7 | Breast | RPMI + 10% FBS + 1% GlutaMAX ™ + 1% Pen/Strep | 5000 |
| MDA-MB-231 | Breast | DMEM + 10% FBS + 1% GlutaMAX ™ + 1% Pen/Strep | 6000 |
| MES-SA | Uterus | RPMI + 10% FBS + 1% GlutaMAX ™ + 1% Pen/Strep | 5000 |
| NCI-H460 | Lung | RPMI + 10% FBS + 1% GlutaMAX ™ + 1% Pen/Strep | 400 |
| NCI-H82 | Lung | RPMI + 10% FBS + 1% GlutaMAX ™ + 1% Pen/Strep | 25000 |
| PC-3 | Prostate | RPMI + 10% FBS + 1% GlutaMAX ™ + 1% Pen/Strep | 2500 |
| Raji | Leukaemia | RPMI + 10% FBS + 1% GlutaMAX ™ + 1% Pen/Strep | 3000 |
| SK-OV-3 | Ovary | RPMI + 10% FBS + 1% GlutaMAX ™ + 1% Pen/Strep | 1500 |
| SNB-19 | Brain | DMEM + 10% FBS + 1% GlutaMAX ™ + 1% Pen/Strep | 600 |
| U-87-MG | Brain | MEM + 10% FBS + 1% GlutaMAX ™ + 1% Pen/Strep | 1500 |

All following cell lines were sourced from American Type Culture Collection (ATCC) (Rockville, MD, USA): 786-0, ACHN, BT-474, DAOY, DU 145, G-361, HCT 116, HCT-15, Hep3B2.1-7, HL-60, HT-1080, HT-29, MCF-7, MDA-MB-231, MES-SA, NCI-H460, NCI-H82, PC-3, Raji, SK-OV-3, U-87 MG.

The A2780 cell line was sourced from the National Cancer Institute (NCI) (Bethesda, MD, USA).

Test Article Formulation

Trypsinogen and Chymotrypsinogen were dissolved directly in the appropriate cell culture medium and immediately added to the cells.

Cell Growth Assays

For combination assays, Test Articles were added to cells 24 hours post-seeding. Test Article concentrations were tested in triplicate for each cell line. Seventy-two hours post addition of Test Articles, the CellTiter-Blue® Assay was carried out on all plates.

The concentration of Trypsinogen used in the combination assays was based on a calculated $IC_{50}$ from single Test Article experiments. The concentration of Trypsinogen for each individual cell line determined the concentration of Chymotrypsinogen at the following ratios: 1:1, 1:2, 1:4, 1:6, 1:8 and 1:10 (Trypsinogen:Chymotrypsinogen). Controls consisted of growth medium only and untreated cells plus growth medium (untreated control).

Assay controls used were growth medium control as a vehicle and growth-medium only (background) as opposed to phosphate-buffered saline control as vehicle and Triton-x 100 as positive control. Background subtraction was not performed for the determination of $IC_{50}$ values.

Following incubation of cells in Test Article-containing media, 10 µL of CellTiter-Blue® was added to each well, then incubated with cells for up to 6 hours. Fluorescence was measured using a Spectramax Gemini XPS Fluorometer (560 nm excitation, 590 nm emission). All data were recorded and entered into Microsoft® Excel spreadsheets for interpretation.

Calculations

Data collected from CellTiter-Blue® assays were plotted as dose response curves for $IC_{50}$ determination. Relative Fluorescence Units (RFU) were plotted against compound concentrations. In these plots, the X-axis (compound concentration) was represented in a logarithmic scale. $IC_{50}$ concentration was calculated as the half maximal (50%) inhibitory concentration (IC) for each compound via a variable slope curve-fitting algorithm using GraphPad Prism version 6.0e for Mac OSX (GraphPad Software, San Diego California, USA).

For combination studies, the coefficient of drug interaction (CDI) was calculated according to the following equation:

$$CDI = \frac{TC}{T \times C}$$

where TC is the growth inhibition of the combination of Trypsinogen and Chymotrypsinogen, T is the growth inhibition of the single agent Trypsinogen and C the growth inhibition of the single agent Chymotrypsinogen. CDI values below 1 indicate drug synergism, whereas values above 1 indicate an antagonistic interaction of Trypsinogen and Chymotrypsinogen.

Cell Growth Inhibition by Trypsinogen and Chymotrypsinogen in Human Cancer

Figure 12:
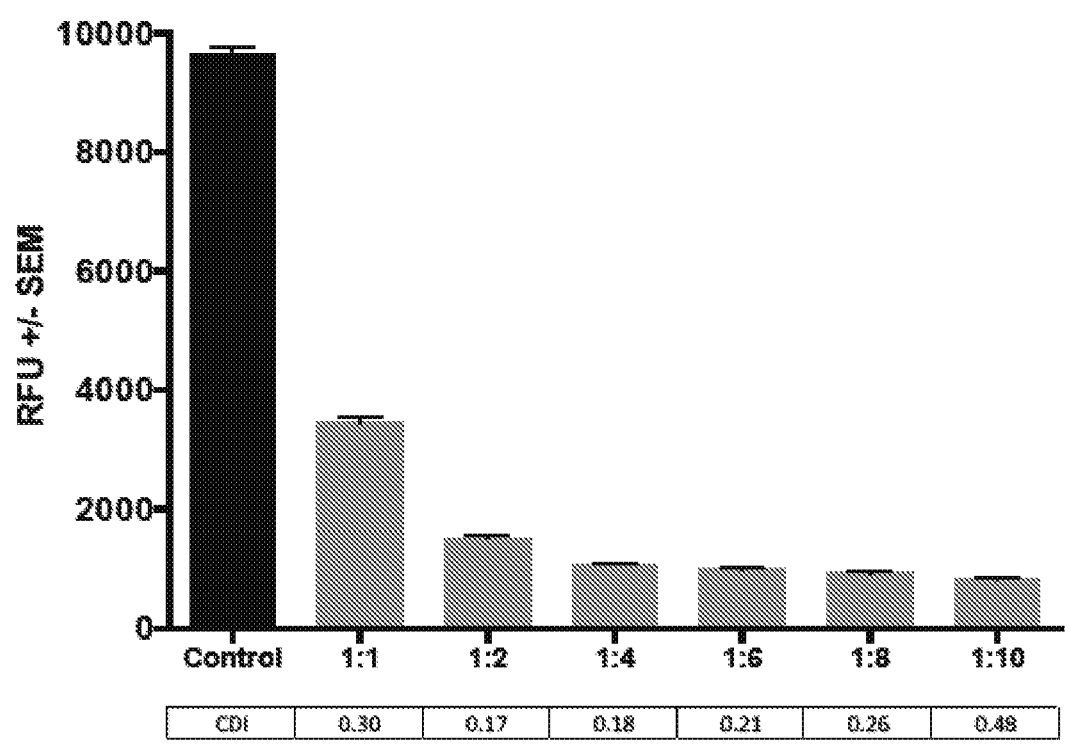
FIG. 12: The effect of Trypsinogen and Chymotrypsinogen alone or in combination on the growth of A2780 human ovary tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (3.174 mg/ml). CDI values were calculated as described.

The effect of Trypsinogen (T) and Chymotrypsinogen (C) alone or in combination on the growth of A2780 ovary tumour cells is shown in FIG. 12. The greatest level of growth inhibition of A2780 ovary tumour cells was observed for ratios greater than 1:8 (T:C), for example 1:10 (T:C), see Table 13 (immediately below).

| A2780 | Replicates (RFU) | | | | | Growth | |
|---|---|---|---|---|---|---|---|
| | 1 | 2 | 3 | Average | SEM | Inhibition | CDI |
| 1x Trypsinogen | 10871.031 | 10998.869 | 11247.885 | 11039.26 | 110.65 | 1.14 | |
| 1x Chymotrypsinogen | 9854.075 | 10037.875 | 9934.535 | 9942.16 | 53.20 | 1.03 | |
| 2x Chymotrypsinogen | 7368.414 | 7412.912 | 8284.251 | 7688.53 | 298.14 | 0.80 | |
| 4x Chymotrypsinogen | 5161.410 | 4959.459 | 5351.289 | 5157.39 | 113.13 | 0.53 | — |
| 6x Chymotrypsinogen | 4068.919 | 3861.354 | 4293.539 | 4074.60 | 124.79 | 0.42 | |
| 8x Chymotrypsinogen | 3145.061 | 2976.396 | 3189.652 | 3103.70 | 64.94 | 0.32 | |
| 10x Chymotrypsinogen | 1531.170 | 1467.334 | 1503.991 | 1500.83 | 18.50 | 0.16 | |
| 1:1 | 3569.706 | 3268.046 | 3522.157 | 3453.30 | 93.64 | 0.36 | 0.30 |
| 1:2 | 1473.600 | 1497.48 | 1592.828 | 1521.30 | 36.42 | 0.16 | 0.17 |
| 1:4 | 1060.256 | 1063.304 | 1112.314 | 1078.62 | 16.87 | 0.11 | 0.18 |
| 1:6 | 1012.297 | 992.679 | 994.430 | 999.80 | 6.27 | 0.10 | 0.21 |
| 1:8 | 959.808 | 879.302 | 939.566 | 926.23 | 24.18 | 0.10 | 0.26 |
| 1:10 | 873.868 | 861.811 | 758.019 | 831.23 | 36.77 | 0.09 | 0.48 |
| Control (cells only) | 9456.568 | 9771.397 | 9750.574 | 9659.51 | 101.65 | | |
| Medium only | 721.110 | 709.561 | 680.464 | 703.71 | 12.09 | — | |

Figure 13:
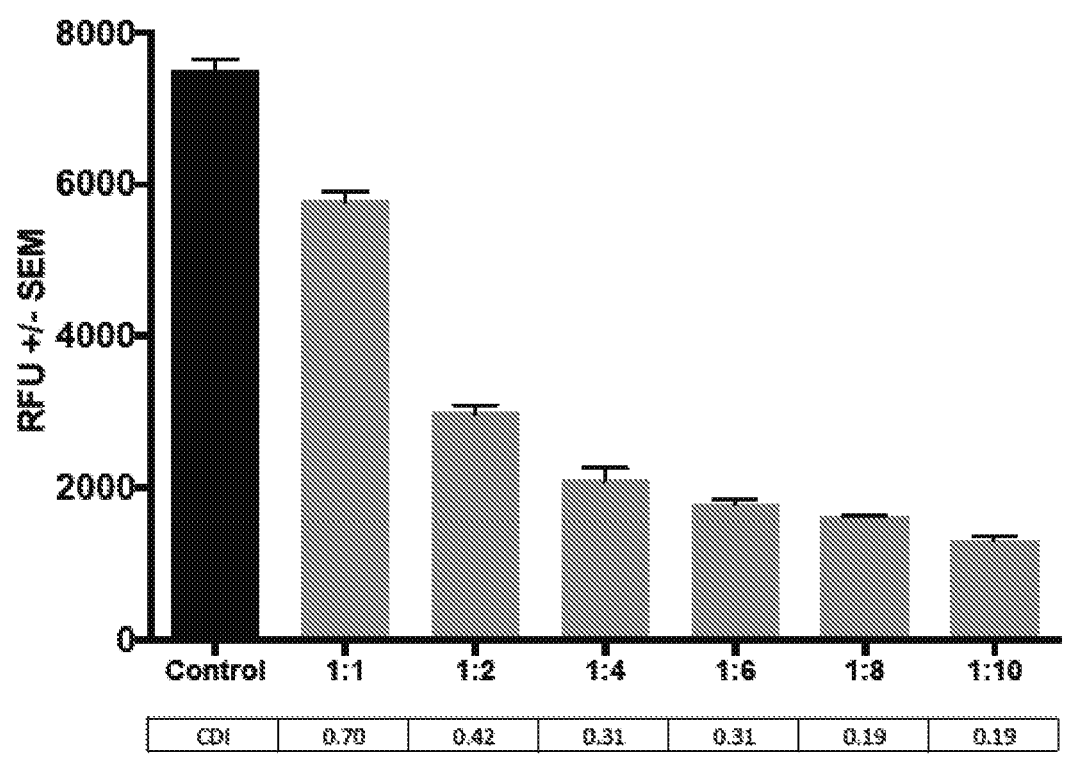
FIG. 13: The effect of Trypsinogen and Chymotrypsinogen alone or in combination on the growth of C8161.9 human melanoma cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (3.917 mg/ml). CDI values were calculated as described.

The effect of Trypsinogen and Chymotrypsinogen alone or in combination on the growth of C8161.9 melanoma cells is shown in FIG. 13. The greatest level of growth inhibition of C8161.9 melanoma cells was observed for ratios greater than 1:8 (T:C), for example 1:10 (T:C), see Table 14 (immediately below).

| C8161.9 | Replicates (RFU) | | | | | Growth | |
|---|---|---|---|---|---|---|---|
| | 1 | 2 | 3 | Average | SEM | Inhibition | CDI |
| 1x Trypsinogen | 8522.324 | 7631.593 | 8520.562 | 8224.83 | 296.62 | 1.10 | |
| 1x Chymotrypsinogen | 6777.939 | 8093.121 | 7808.435 | 7559.83 | 399.49 | 1.01 | |
| 2x Chymotrypsinogen | 6077.701 | 6742.977 | 6393.707 | 6404.80 | 192.13 | 0.85 | |
| 4x Chymotrypsinogen | 6515.904 | 6079.726 | 5879.160 | 6158.26 | 187.96 | 0.82 | — |
| 6x Chymotrypsinogen | 5416.613 | 5005.616 | 5229.323 | 5217.18 | 118.80 | 0.69 | |
| 8x Chymotrypsinogen | 7333.727 | 8090.684 | 8238.635 | 7887.68 | 280.25 | 1.05 | |
| 10x Chymotrypsinogen | 5673.008 | 6755.334 | 6653.124 | 6360.49 | 345.00 | 0.85 | |
| 1:1 | 5554.142 | 5775.944 | 6000.930 | 5777.01 | 128.98 | 0.77 | 0.70 |
| 1:2 | 3153.882 | 2757.958 | 3030.887 | 2980.91 | 116.99 | 0.40 | 0.42 |

-continued

| C8161.9 | Replicates (RFU) | | | Average | SEM | Growth Inhibition | CDI |
|---|---|---|---|---|---|---|---|
| | 1 | 2 | 3 | | | | |
| 1:4 | 1917.887 | 1922.872 | 2423.867 | 2088.21 | 167.84 | 0.28 | 0.31 |
| 1:6 | 1722.204 | 1741.576 | 1894.141 | 1785.97 | 54.37 | 0.24 | 0.31 |
| 1:8 | 1611.822 | 1638.031 | 1620.716 | 1623.52 | 7.69 | 0.22 | 0.19 |
| 1:10 | 1321.071 | 1166.744 | 1424.934 | 1304.25 | 75.01 | 0.17 | 0.19 |
| Control (cells only) | 7676.335 | 7617.46 | 7233.554 | 7509.12 | 138.83 | | |
| Medium only | 701.358 | 680.206 | 678.760 | 686.77 | 7.30 | — | |

Figure 14:
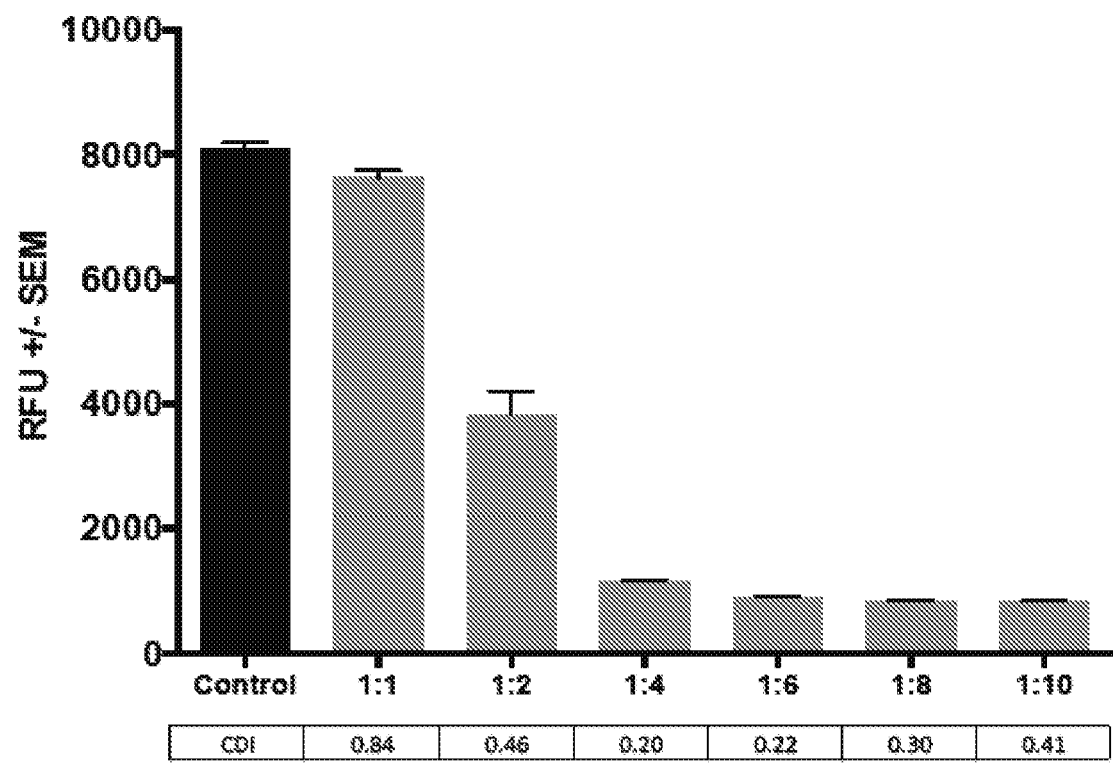
FIG. 14: The effect of Trypsinogen and Chymotrypsinogen alone or in combination on the growth of DAOY human brain tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (2.654 mg/ml). CDI values were calculated as described.

The effect of Trypsinogen and Chymotrypsinogen alone or in combination on the growth of DAOY brain tumour cells shown in FIG. 14. The greatest level of growth inhibition of DAOY brain tumour cells was observed for ratios greater than 1:8 (T:C), for example 1:10 (T:C), see Table 15 (immediately below).

| DAOY | Replicates (RFU) | | | Average | SEM | Growth Inhibition | CDI |
|---|---|---|---|---|---|---|---|
| | 1 | 2 | 3 | | | | |
| 1x Trypsinogen | 9051.549 | 9141.617 | 8347.920 | 8847.03 | 250.91 | 1.09 | |
| 1x Chymotrypsinogen | 8285.778 | 8192.939 | 8384.539 | 8287.75 | 55.32 | 1.02 | |
| 2x Chymotrypsinogen | 7865.063 | 7416.132 | 7612.021 | 7631.07 | 129.94 | 0.94 | |
| 4x Chymotrypsinogen | 5604.916 | 5300.233 | 5226.702 | 5377.28 | 115.78 | 0.66 | — |
| 6x Chymotrypsinogen | 4077.504 | 3677.683 | 3736.964 | 3830.72 | 124.57 | 0.47 | |
| 8x Chymotrypsinogen | 2896.918 | 2564.253 | 2455.450 | 2638.87 | 132.79 | 0.33 | |
| 10x Chymotrypsinogen | 1487.412 | 2023.845 | 2125.137 | 1878.80 | 197.87 | 0.23 | |
| 1:1 | 7861.021 | 7507.552 | 7543.847 | 7637.47 | 112.26 | 0.94 | 0.84 |
| 1:2 | 3425.338 | 3528.294 | 4562.312 | 3838.65 | 363.05 | 0.47 | 0.46 |
| 1:4 | 1142.231 | 1203.894 | 1154.619 | 1166.91 | 18.83 | 0.14 | 0.20 |
| 1:6 | 931.248 | 919.907 | 885.739 | 912.30 | 13.68 | 0.11 | 0.22 |
| 1:8 | 836.923 | 876.032 | 850.750 | 854.57 | 11.45 | 0.11 | 0.30 |
| 1:10 | 853.177 | 835.564 | 833.322 | 840.69 | 6.28 | 0.10 | 0.41 |
| Control (cells only) | 7932.601 | 8226.676 | 8164.348 | 8107.88 | 89.46 | | |
| Medium only | 771.175 | 766.154 | 457.132 | 664.82 | 103.85 | — | |

Figure 15:
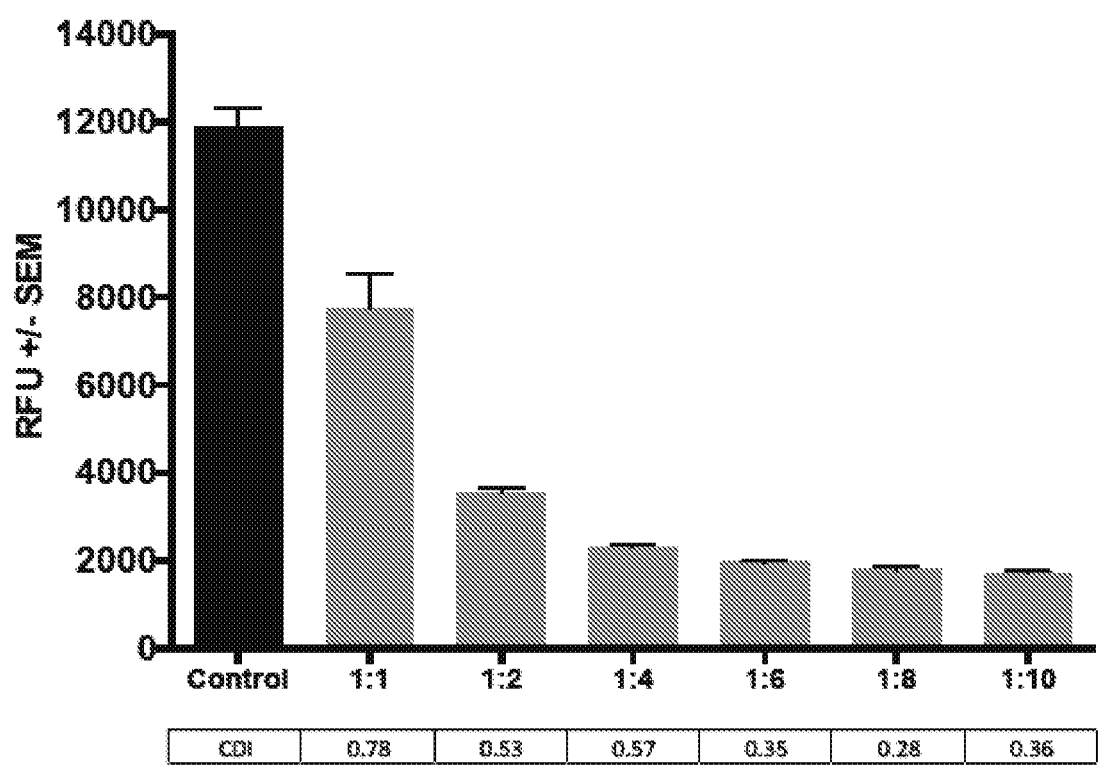
FIG. 15: The effect of Trypsinogen and Chymotrypsinogen alone or in combination on the growth of DU145 human prostate tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (3.843 mg/ml). CDI values were calculated as described.

The effect of Trypsinogen and Chymotrypsinogen alone or in combination on the growth of DU145 prostate tumour cells shown in FIG. 15. The greatest level of growth inhibition of DU145 prostate tumour cells was observed for ratios greater than 1:8 (T:C), for example 1:10 (T:C), see Table 16 (immediately below).

| DU145 | Replicates (RFU) | | | Average | SEM | Growth Inhibition | CDI |
|---|---|---|---|---|---|---|---|
| | 1 | 2 | 3 | | | | |
| 1x Trypsinogen | 12316.109 | 12798.373 | 11894.605 | 12336.36 | 261.09 | 1.04 | |
| 1x Chymotrypsinogen | 9641.914 | 9745.273 | 9408.376 | 9598.52 | 99.64 | 0.81 | |
| 2x Chymotrypsinogen | 6119.162 | 6511.184 | 6872.414 | 6500.92 | 217.51 | 0.55 | |
| 4x Chymotrypsinogen | 4067.276 | 4021.511 | 3791.056 | 3959.95 | 85.47 | 0.33 | — |
| 6x Chymotrypsinogen | 6162.657 | 6462.893 | 3916.473 | 5514.01 | 803.46 | 0.46 | |
| 8x Chymotrypsinogen | 6200.357 | 6068.926 | 6238.773 | 6169.35 | 51.42 | 0.52 | |
| 10x Chymotrypsinogen | 5037.879 | 4455.197 | 4268.117 | 4587.06 | 231.79 | 0.39 | |
| 1:1 | 8125.897 | 6246.690 | 8858.232 | 7743.61 | 777.74 | 0.65 | 0.78 |
| 1:2 | 3680.328 | 3374.181 | 3633.843 | 3562.78 | 95.25 | 0.30 | 0.53 |
| 1:4 | 2269.460 | 2366.647 | 2364.699 | 2333.60 | 32.08 | 0.20 | 0.57 |
| 1:6 | 1943.051 | 2036.505 | 1959.739 | 1979.77 | 28.78 | 0.17 | 0.35 |
| 1:8 | 1838.590 | 1705.612 | 1888.048 | 1810.75 | 54.47 | 0.15 | 0.28 |
| 1:10 | 1786.460 | 1756.369 | 1675.614 | 1739.48 | 33.09 | 0.15 | 0.36 |
| Control (cells only) | 12466.964 | 12147.758 | 10992.462 | 11869.06 | 447.88 | | |
| Medium only | 893.398 | 833.691 | 828.200 | 851.76 | 20.88 | — | |

Figure 16:
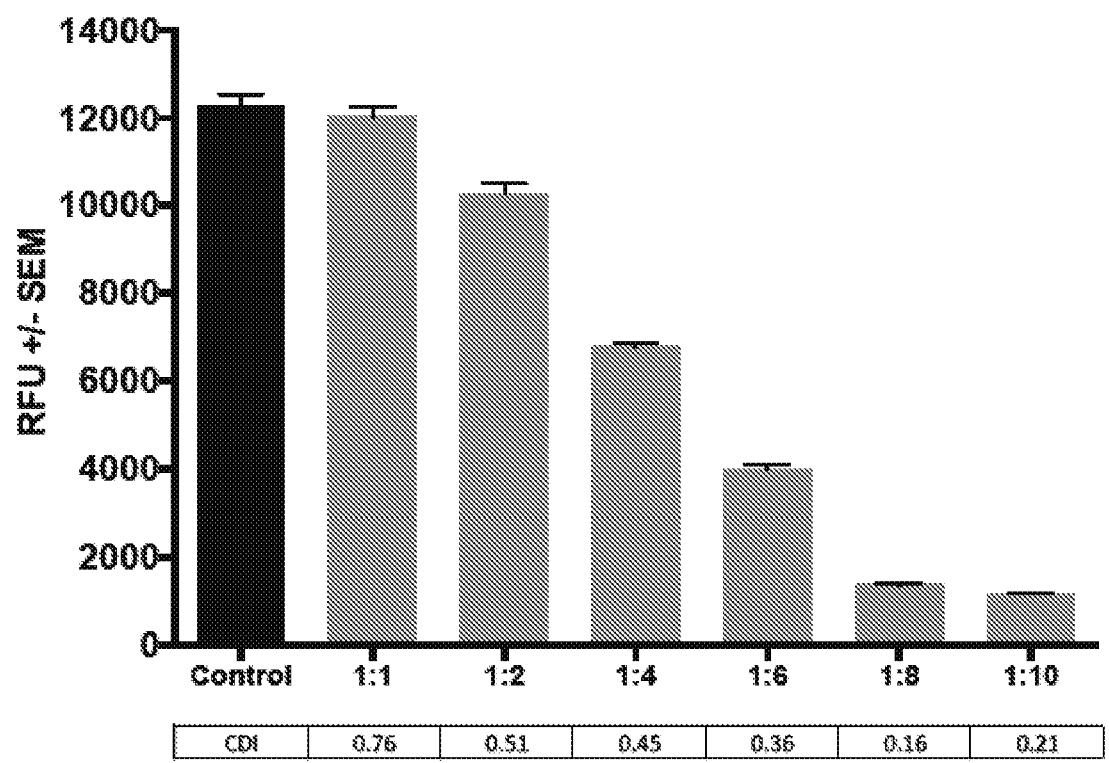
FIG. 16: The effect of Trypsinogen and Chymotrypsinogen alone or in combination on the growth of HCT 116 human colorectal tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (16.43 mg/ml). CDI values were calculated as described.

The effect of Trypsinogen and Chymotrypsinogen alone or in combination on the growth of HCT 116 colorectal tumour cells shown in FIG. 16. The greatest level of growth inhibition of HCT 116 colorectal tumour cells was observed for ratios greater than 1:8 (T:C), for example 1:10 (T:C), see Table 17 (immediately below).

|  | Replicates (RFU) | | | | | Growth | |
| --- | --- | --- | --- | --- | --- | --- | --- |
| HCT 116 | 1 | 2 | 3 | Average | SEM | Inhibition | CDI |
| 1x Trypsinogen | 14859.604 | 15104.608 | 16112.500 | 15358.90 | 383.38 | 1.25 | |
| 1x Chymotrypsinogen | 12051.548 | 12853.539 | 13225.642 | 12710.24 | 346.42 | 1.04 | |
| 2x Chymotrypsinogen | 15683.443 | 16403.678 | 16092.573 | 16059.90 | 208.55 | 1.31 | |
| 4x Chymotrypsinogen | 11913.774 | 12127.43 | 11827.383 | 11956.20 | 89.18 | 0.97 | — |
| 6x Chymotrypsinogen | 8377.944 | 8716.581 | 9240.221 | 8778.25 | 250.82 | 0.71 | |
| 8x Chymotrypsinogen | 6522.517 | 6712.549 | 6865.853 | 6700.31 | 99.30 | 0.55 | |
| 10x Chymotrypsinogen | 4346.238 | 4803.888 | 4534.618 | 4561.58 | 132.80 | 0.37 | |
| 1:1 | 12396.237 | 12051.078 | 11672.182 | 12039.83 | 209.09 | 0.98 | 0.76 |
| 1:2 | 10120.919 | 10732.156 | 10003.201 | 10285.43 | 225.94 | 0.84 | 0.51 |
| 1:4 | 6582.828 | 6926.802 | 6857.768 | 6789.13 | 105.06 | 0.55 | 0.45 |
| 1:6 | 4158.295 | 3803.743 | 3997.355 | 3986.46 | 102.50 | 0.32 | 0.36 |
| 1:8 | 1306.618 | 1395.309 | 1404.950 | 1368.96 | 31.29 | 0.11 | 0.16 |
| 1:10 | 1173.282 | 1172.682 | 1199.737 | 1181.90 | 8.92 | 0.10 | 0.21 |
| Control (cells only) | 11788.172 | 12334.407 | 12717.700 | 12280.09 | 269.70 | | |
| Medium only | 853.945 | 862.254 | 852.246 | 856.15 | 3.09 | — | |

Figure 17:
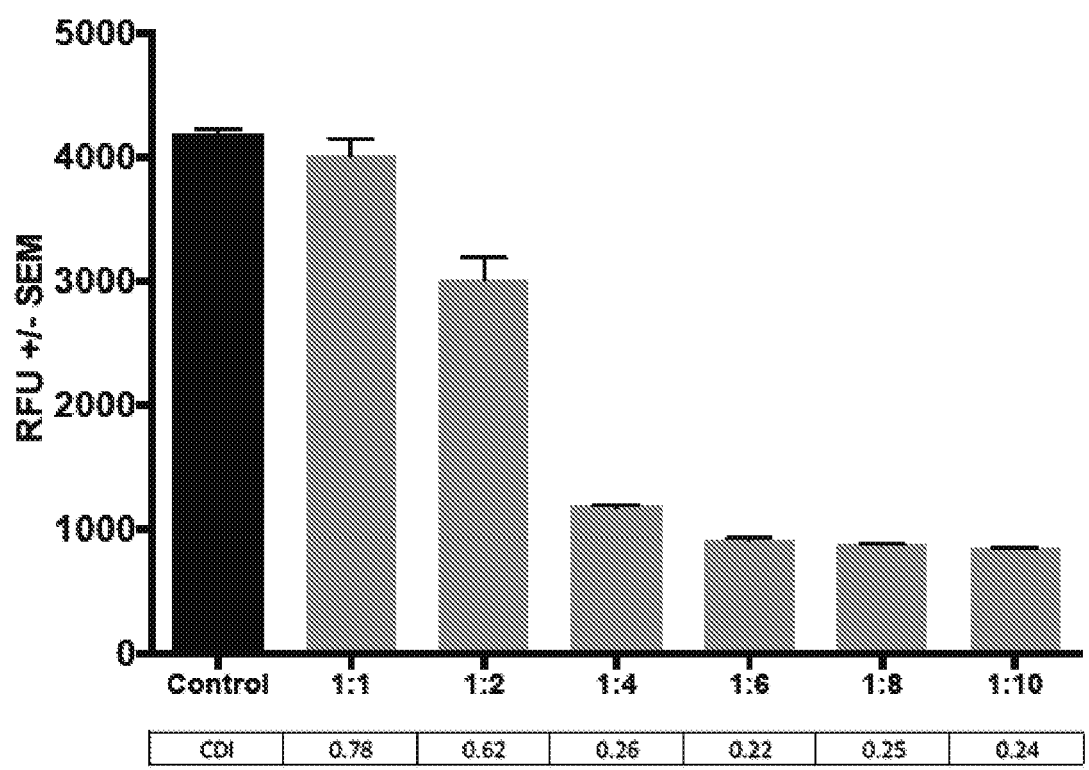
FIG. 17: The effect of Trypsinogen and Chymotrypsinogen alone or in combination on the growth of Hep3B2.1-7 human liver tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (2.483 mg/ml). CDI values were calculated as described.

The effect of Trypsinogen and Chymotrypsinogen alone or in combination on the growth of Hep3B2.1-7 liver tumour cells shown in FIG. 17. The greatest level of growth inhibition of Hep3B2.1-7 liver tumour cells was observed for ratios greater than 1:8 (T:C), for example 1:10 (T:C), see Table 18 (immediately below).

|  | Replicates (RFU) | | | | | Growth | |
| --- | --- | --- | --- | --- | --- | --- | --- |
| Hep3B2.1-7 | 1 | 2 | 3 | Average | SEM | Inhibition | CDI |
| 1x Trypsinogen | 5763.579 | 5761.003 | 5278.852 | 5601.14 | 161.15 | 1.34 | |
| 1x Chymotrypsinogen | 3690.053 | 3975.591 | 3801.437 | 3822.36 | 83.09 | 0.92 | |
| 2x Chymotrypsinogen | 3829.325 | 3508.687 | 3595.125 | 3644.38 | 95.78 | 0.87 | |
| 4x Chymotrypsinogen | 3349.295 | 3516.303 | 3482.731 | 3449.44 | 51.00 | 0.83 | — |
| 6x Chymotrypsinogen | 3271.956 | 3098.025 | 3087.413 | 3152.46 | 59.82 | 0.75 | |
| 8x Chymotrypsinogen | 2348.604 | 2595.240 | 2850.457 | 2598.10 | 144.88 | 0.62 | |
| 10x Chymotrypsinogen | 2513.241 | 2617.293 | 2788.512 | 2639.68 | 80.25 | 0.63 | |
| 1:1 | 3980.236 | 4263.435 | 3773.279 | 4005.65 | 142.07 | 0.96 | 0.78 |
| 1:2 | 3308.778 | 2702.337 | 3030.569 | 3013.89 | 175.26 | 0.72 | 0.62 |
| 1:4 | 1182.575 | 1158.461 | 1209.168 | 1183.40 | 14.64 | 0.28 | 0.26 |
| 1:6 | 937.534 | 893.343 | 919.586 | 916.82 | 12.83 | 0.22 | 0.22 |
| 1:8 | 863.658 | 868.435 | 894.195 | 875.43 | 9.48 | 0.21 | 0.25 |
| 1:10 | 862.721 | 844.240 | 857.605 | 854.86 | 5.51 | 0.20 | 0.24 |
| Control (cells only) | 4078.486 | 4214.781 | 4236.280 | 4176.52 | 49.41 | | |
| Medium only | 695.284 | 697.555 | 695.303 | 696.05 | 0.75 | — | |

Figure 18:
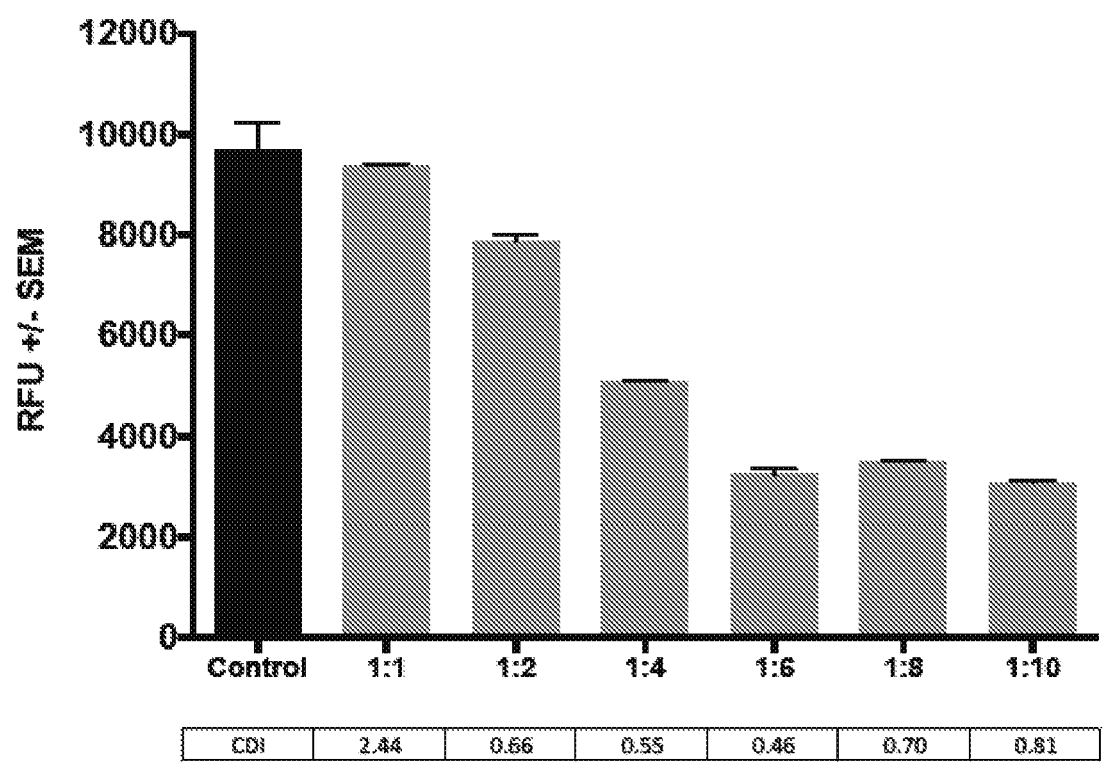
FIG. 18: The effect of Trypsinogen and Chymotrypsinogen alone or in combination on the growth of HT-29 human colorectal tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (15.12 mg/ml). CDI values were calculated as described.

The effect of Trypsinogen and Chymotrypsinogen alone or in combination on the growth of HT-29 colorectal tumour cells shown in FIG. 18. The greatest level of growth inhibition of HT-29 colorectal tumour cells was observed for ratios greater than 1:8 (T:C), for example 1:10 (T:C), see Table 19 (immediately below).

|  | Replicates (RFU) | | | | | Growth | |
| --- | --- | --- | --- | --- | --- | --- | --- |
| HT-29 | 1 | 2 | 3 | Average | SEM | Inhibition | CDI |
| 1x Trypsinogen | 8223.840 | 8376.067 | 8518.233 | 8372.71 | 85.00 | 0.86 | |
| 1x Chymotrypsinogen | 4538.796 | 4481.600 | 4338.855 | 4453.08 | 59.45 | 0.46 | |
| 2x Chymotrypsinogen | 13525.958 | 14096.041 | 13637.257 | 13753.09 | 174.46 | 1.42 | |
| 4x Chymotrypsinogen | 10580.120 | 10971.600 | 10771.067 | 10774.26 | 113.02 | 1.11 | — |
| 6x Chymotrypsinogen | 8547.735 | 7930.625 | 8223.705 | 8234.02 | 178.22 | 0.85 | |
| 8x Chymotrypsinogen | 5538.742 | 6045.101 | 5833.865 | 5805.90 | 146.84 | 0.60 | |
| 10x Chymotrypsinogen | 4538.783 | 4299.262 | 4388.604 | 4408.88 | 69.88 | 0.45 | |
| 1:1 | 9352.964 | 9423.387 | 9389.121 | 9388.49 | 20.33 | 0.97 | 2.44 |
| 1:2 | 7848.395 | 7681.472 | 8119.716 | 7883.19 | 127.70 | 0.81 | 0.66 |
| 1:4 | 5051.926 | 5072.896 | 5130.757 | 5085.19 | 23.57 | 0.52 | 0.55 |
| 1:6 | 3426.633 | 3235.928 | 3040.573 | 3234.38 | 111.45 | 0.33 | 0.46 |
| 1:8 | 3505.802 | 3421.350 | 3548.355 | 3491.84 | 37.32 | 0.36 | 0.70 |
| 1:10 | 3010.496 | 3166.377 | 3032.058 | 3069.64 | 48.77 | 0.32 | 0.81 |

-continued

| HT-29 | Replicates (RFU) | | | Average | SEM | Growth Inhibition | CDI |
|---|---|---|---|---|---|---|---|
| | 1 | 2 | 3 | | | | |
| Control (cells only) | 8815.367 | 9695.704 | 10592.513 | 9701.19 | 513.03 | | |
| Medium only | 812.770 | 807.322 | 813.374 | 811.16 | 1.92 | — | |

Figure 19:
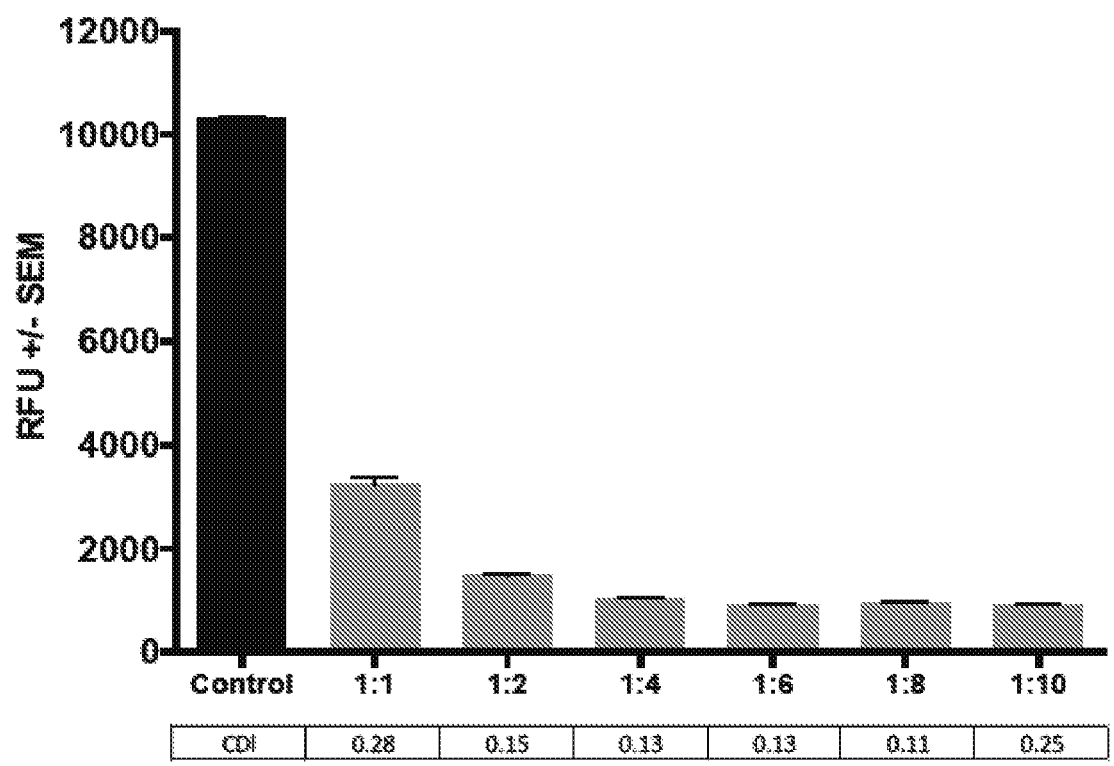
FIG. 19: The effect of Trypsinogen and Chymotrypsinogen alone or in combination on the growth of HuH-7 human liver tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (3.934 mg/ml). CDI values were calculated as described.

The effect of Trypsinogen and Chymotrypsinogen alone or in combination on the growth of HuH-7 liver tumour cells shown in FIG. 19. The greatest level of growth inhibition of HuH-7 liver tumour cells was observed for ratios greater than 1:8 (T:C), for example 1:10 (T:C), see Table 20 (immediately below).

| HuH-7 | Replicates (RFU) | | | Average | SEM | Growth Inhibition | CDI |
|---|---|---|---|---|---|---|---|
| | 1 | 2 | 3 | | | | |
| 1x Trypsinogen | 11847.077 | 11647.785 | 11902.568 | 11799.14 | 77.36 | 1.14 | |
| 1x Chymotrypsinogen | 9654.204 | 9996.031 | 10270.954 | 9973.73 | 178.39 | 0.97 | |
| 2x Chymotrypsinogen | 8675.452 | 8331.810 | 9428.336 | 8811.87 | 323.80 | 0.85 | |
| 4x Chymotrypsinogen | 7352.330 | 6400.635 | 7106.839 | 6953.27 | 285.26 | 0.67 | — |
| 6x Chymotrypsinogen | 6385.941 | 6303.662 | 6554.035 | 6414.55 | 73.68 | 0.62 | |
| 8x Chymotrypsinogen | 7693.982 | 7100.407 | 7891.567 | 7561.99 | 237.73 | 0.73 | |
| 10x Chymotrypsinogen | 3056.197 | 3186.256 | 3368.272 | 3203.58 | 90.50 | 0.31 | |
| 1:1 | 3151.837 | 2987.080 | 3515.283 | 3218.07 | 156.03 | 0.31 | 0.28 |
| 1:2 | 1513.124 | 1461.279 | 1502.350 | 1492.25 | 15.80 | 0.14 | 0.15 |
| 1:4 | 1020.535 | 1034.911 | 1061.719 | 1039.06 | 12.07 | 0.10 | 0.13 |
| 1:6 | 950.172 | 923.260 | 928.811 | 934.08 | 8.20 | 0.09 | 0.13 |
| 1:8 | 962.377 | 980.744 | 969.830 | 970.98 | 5.33 | 0.09 | 0.11 |
| 1:10 | 943.712 | 902.317 | 924.857 | 923.63 | 11.97 | 0.09 | 0.25 |
| Control (cells only) | 10366.099 | 10304.473 | 10314.27 | 10328.28 | 19.12 | | |
| Medium only | 783.754 | 745.053 | 749.117 | 759.31 | 12.28 | — | |

Figure 20:
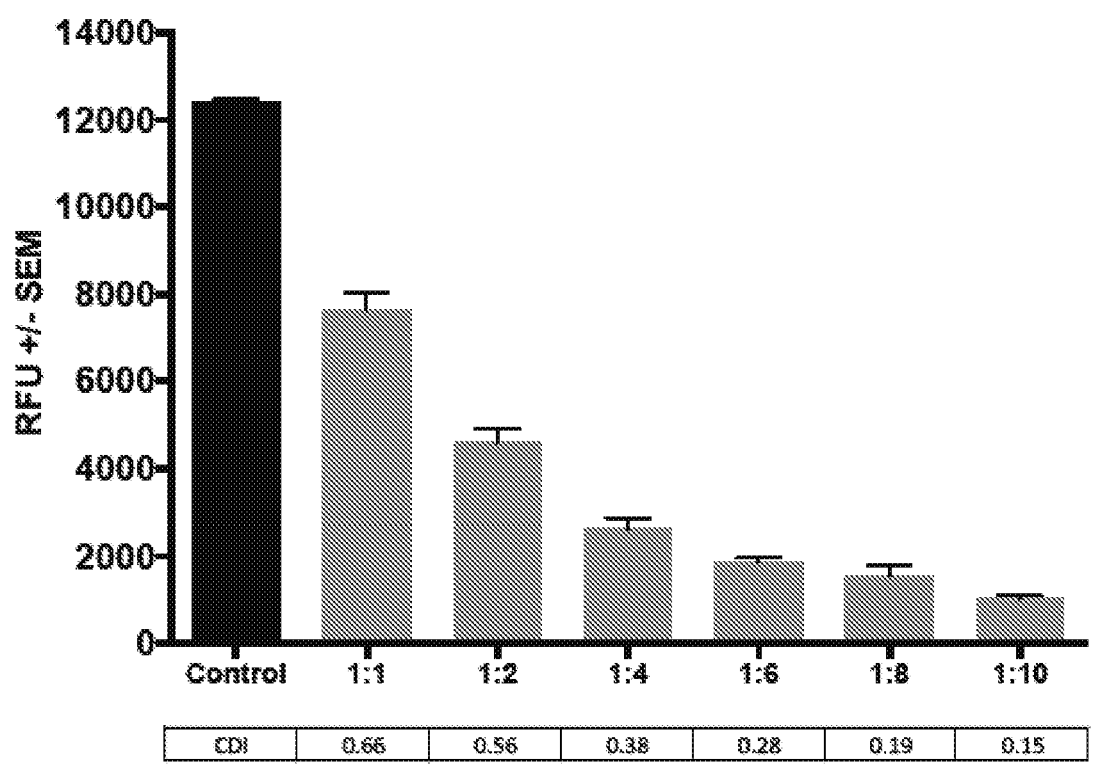
FIG. 20: The effect of Trypsinogen and Chymotrypsinogen alone or in combination on the growth of NCI-H460 human lung tumour cells. Combination assays of Trypsinogen and Chymotrypsinogen were performed at ratios of 1:1, 1:2, 1:4, 1:6, 1:8 and 1:10 based on the previously determined $IC_{50}$ of Trypsinogen (4.028 mg/ml). CDI values were calculated as described.

The effect of Trypsinogen and Chymotrypsinogen alone or in combination on the growth of NCI-H460 lung tumour cells shown in FIG. 20. The greatest level of growth inhibition of NCI-H460 lung tumour cells was observed for ratios greater than 1:8 (T:C), for example 1:10 (T:C), see Table 21 (immediately below).

| NCI-H460 | Replicates (RFU) | | | Average | SEM | Growth Inhibition | CDI |
|---|---|---|---|---|---|---|---|
| | 1 | 2 | 3 | | | | |
| 1x Trypsinogen | 12766.405 | 13907.190 | 13715.400 | 13463.00 | 352.67 | 1.08 | |
| 1x Chymotrypsinogen | 9938.641 | 11144.394 | 11179.673 | 10754.24 | 407.92 | 0.87 | |
| 2x Chymotrypsinogen | 7917.386 | 6785.913 | 7954.079 | 7552.46 | 383.42 | 0.61 | |
| 4x Chymotrypsinogen | 6269.978 | 6384.694 | 6637.457 | 6430.71 | 108.55 | 0.52 | — |
| 6x Chymotrypsinogen | 6382.878 | 5722.162 | 6237.417 | 6114.15 | 200.44 | 0.49 | |
| 8x Chymotrypsinogen | 7626.570 | 8267.497 | 7096.047 | 7663.37 | 338.67 | 0.62 | |
| 10x Chymotrypsinogen | 6828.383 | 5910.312 | 6399.807 | 6379.50 | 265.22 | 0.51 | |
| 1:1 | 7832.132 | 6908.952 | 8165.215 | 7635.43 | 375.75 | 0.61 | 0.66 |
| 1:2 | 4780.923 | 5036.047 | 4030.338 | 4615.77 | 301.84 | 0.37 | 0.56 |
| 1:4 | 3010.435 | 2684.551 | 2205.659 | 2633.55 | 233.71 | 0.21 | 0.38 |
| 1:6 | 1976.275 | — | 1786.417 | 1285.22 | 94.93 | 0.15 | 0.28 |
| 1:8 | 1589.983 | 1128.840 | 1940.589 | 1553.14 | 235.05 | 0.12 | 0.19 |
| 1:10 | 1021.508 | 1142.525 | 954.422 | 1039.49 | 55.04 | 0.08 | 0.15 |
| Control (cells only) | 12357.635 | 12437.118 | 12494.679 | 12429.81 | 39.73 | | |
| Medium only | 859.583 | 856.347 | 840.046 | 851.99 | 6.05 | — | |

The invention claimed is:

1. A method of treating cancer in a subject comprising administering chymotrypsinogen in an amount of 41 mg/kg and trypsinogen in an amount of is 6.75 mg/kg, thereby treating cancer in a subject.

2. The method according to claim 1, wherein the cancer is selected from pancreatic cancer, oesophageal cancer, colon cancer, bowel cancer, prostate cancer, ovarian cancer, stomach cancer, breast cancer, malignant melanoma or lung cancer.

3. The method according to claim 1, wherein the cancer is, ovarian cancer.

4. A method for treating pancreatic cancer in a subject comprising administering chymotrypsinogen in an amount of 41 mg/kg and trypsinogen in an amount of 7 mg/kg, thereby treating pancreatic cancer in the subject.

* * * * *